US009828386B2

(12) United States Patent
Tang et al.

(10) Patent No.: US 9,828,386 B2
(45) Date of Patent: Nov. 28, 2017

(54) SULFUR-SUBSTITUTED PODOPHYLLOTOXIN DERIVATIVE, SYNTHESIS METHOD THEREOF, AND USE THEREOF

(71) Applicant: HUBEI UNIVERSITY OF TECHNOLOGY, Wuhan, Hubei (CN)

(72) Inventors: Yajie Tang, Wuhan (CN); Jianlong Li, Wuhan (CN); Wei Zhao, Wuhan (CN); Hongmei Li, Wuhan (CN)

(73) Assignee: HUBEI UNIVERSITY OF TECHNOLOGY, Wuhan (CN)

( * ) Notice: Subject to any disclaimer, the term of this patent is extended or adjusted under 35 U.S.C. 154(b) by 0 days.

(21) Appl. No.: 15/036,132

(22) PCT Filed: Sep. 5, 2014

(86) PCT No.: PCT/CN2014/085994
§ 371 (c)(1),
(2) Date: May 12, 2016

(87) PCT Pub. No.: WO2015/070661
PCT Pub. Date: May 21, 2015

(65) Prior Publication Data
US 2016/0264592 A1  Sep. 15, 2016

(30) Foreign Application Priority Data
Nov. 15, 2013  (CN) .......................... 2013 1 0571051

(51) Int. Cl.
*C07D 493/04*  (2006.01)

(52) U.S. Cl.
CPC ................................. *C07D 493/04* (2013.01)

(58) Field of Classification Search
CPC ..................................................... C07D 493/04
See application file for complete search history.

(56) References Cited

FOREIGN PATENT DOCUMENTS

| CN | 102757442 A | 10/2012 |
|---|---|---|
| WO | WO 2004/033423 A2 | 4/2004 |

OTHER PUBLICATIONS

Pan et al., "Synthesis and antitumour activity of new derivatives of podophyllotoxin", Current Science, vol. 72, No. 4, Feb. 25, 1997, pp. 268-271.

*Primary Examiner* — Samira Jean-Louis
(74) *Attorney, Agent, or Firm* — Birch, Stewart, Kolasch & Birch, LLP

(57) ABSTRACT

The present invention discloses a sulfur-substituted podophyllotoxin derivative, synthesis method thereof, and use thereof. The present invention introduces a rigid aromatic heterocyclic compound, as well as a further sulfonamidated product of 3-amino-5-mercapto-1,2,4-triazole, 2-amino-5-mercapto-1,3,4-thiadiazole, 4-methylbenzenesulfonyl chloride, or 4-methoxybenzenesulfonyl chloride as a substituent group, into position 4 of the C-ring of podophyllotoxin or 4'-demethylepipodophyllotoxin to obtain the podophyllotoxin derivative shown in formula (V), said derivative having significantly increased antitumor activity and reduced toxic side effects. Experiments on in vitro tumor cell inhibition indicate that the antitumor activity of the compound of formula (V) of the present invention is significantly higher than the antitumor activity of podophyllotoxin or 4'-demethylepipodophyllotoxin.

11 Claims, 3 Drawing Sheets

Podophyllotoxin  4'-Demethylepipodophyllotoxin

SULFUR-SUBSTITUTED PODOPHYLLOTOXIN DERIVATIVE, SYNTHESIS METHOD THEREOF, AND USE THEREOF

TECHNICAL FIELD OF THE INVENTION

Embodiments of the present invention relate to podophyllotoxin-type derivatives and synthetic method thereof, in particular to sulfur-substituted derivatives of podophyllotoxin-type and their synthesis and purification method. Embodiments of the invention further relate to their application in the preparation of anti-tumor drugs, belonging to field of podophyllotoxin-type derivatives.

BACKGROUND OF THE INVENTION

Podophyllotoxin and 4'-demethylepipodophyllotoxin have structures as illustrated on formulas (I) and (II) in FIG. 1; podophyllotoxin and 4'-demethylepipodophyllotoxin are natural active lead compounds with unique anti-tumor activity extracted from podophyllotoxin-type plants (such as Berberidaceae Sinopodophyllum hexandrum, umbrellaleaf, dysosma versipellis etc.), with shortcomings such as strong toxic and side effect and poor bioavailability limiting their clinical application.

SUMMARY OF THE INVENTION

One purpose of the invention is to provide a kind of sulfur-substituted podophyllotoxin-type derivatives with good anti-tumor activity;

Second purpose is to provide a method for preparing or purifying the sulfur-substituted podophyllotoxin derivatives;

Third purpose is to apply the sulfur-substituted podophyllotoxin derivatives to the preparations of the clinical anti-tumor drugs.

The purposes as above are realized by the following technical scheme:

Structural formula of a kind of sulfur-substituted podophyllotoxin derivatives or salts with anti-tumor activity are illustrated on formula (V):

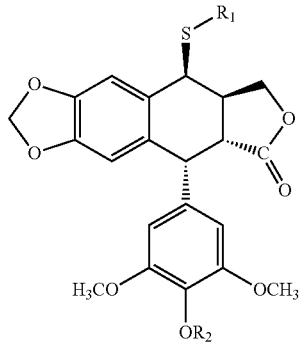

Formula (V)

wherein, R1 is selected from

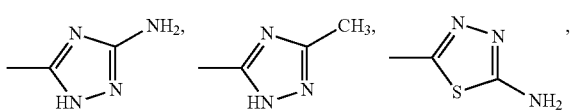

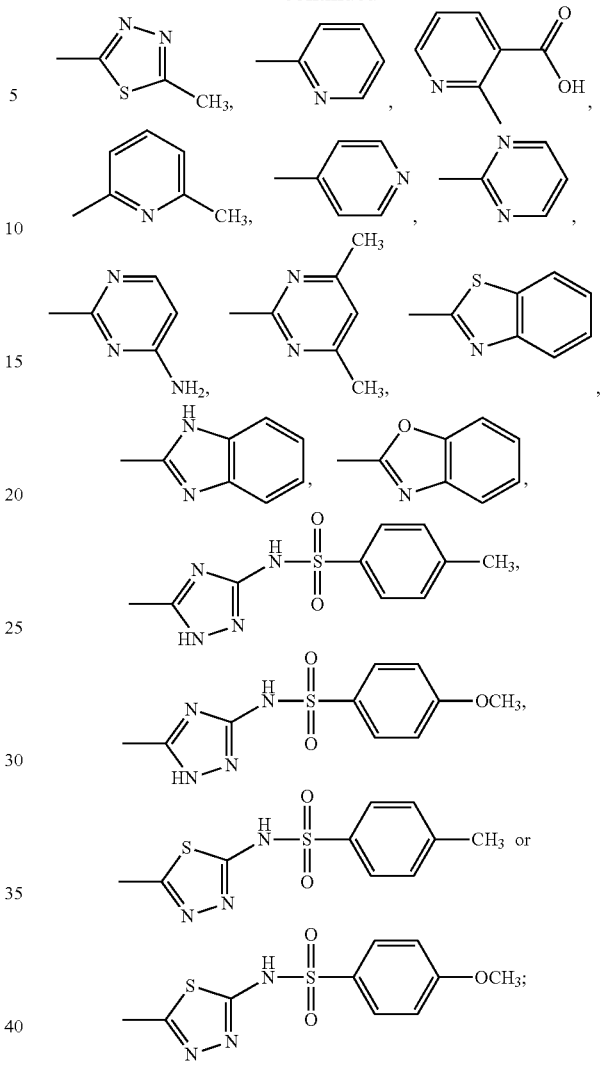

R2 is hydrogen or CH3.

In addition, acid salts of compounds of formula (V) are also included in the scope of embodiments of the present invention. Preferably, the acid salts include hydrochloride, phosphate, and so on.

3-amino-5-mercapto-1,2,4-triazole, 3-mercapto-5-methyl-1,2,4-triazole, 2-amino-5-mercapto-1,3,4-thiadiazole, 2-mercapto-5-methyl-1,3,4-thiadiazole, 2-mercaptopyridine, 2-mercapto-nicotinic acid, 2-mercapto-6-methylpyridine, 4-mercaptopyridine, 2-mercaptopyrimidine, 4-amino-2-mercaptopyrimidine, 4,6-dimethyl-2-mercaptopyrimidine, 2-mercaptobenzothiazole, 2-mercaptobenzimidazole, 2-mercaptobenzoxazole are rigid aromatic heterocyclic compounds as shown in formula (III). By using them as a substituent group, it facilitates formation of position 4 of the C-ring of β configuration of podophyllotoxin and 4'-demethylepipodophyllotoxin. Further sulfonamide product of 3-amino-5-mercapto-1,2,4-triazole, 2-amino-5-mercapto-1,3,4-thiadiazole and 4-methyl benzenesulfonyl chloride or 4-methoxy benzenesulfonyl chloride is intermediate of synthesis of many drugs with anti-tumor activity, with its sulfonamide product as a substituent group, to obtain podophyllotoxins derivatives with further enhanced anti-tumor activity and less toxic and side effect.

The second purpose of embodiment of the invention is to provide a method for preparing compound of above formula (V), comprising the steps of:

by nucleophilic substitution reaction, 3-amino-5-mercapto-1,2,4-triazole, 3-mercapto-5-methyl-1,2,4-triazole, 2-amino-5-mercapto-1,3,4-thiadiazole, 2-mercapto-5-methyl-1,3,4-thiadiazole, 2-mercaptopyridine, 2-mercapto nicotinic acid, 2-mercapto-6-methylpyridine, 4-mercaptopyridine, 2-mercaptopyrimidine, 4-amino-2-mercaptopyrimidine, 4,6-dimethyl-2-mercaptopyrimidine, 2-mercaptobenzothiazole, 2-mercaptobenzimidazole or 2-mercaptobenzoxazole being introduced into position 4 of the C-ring of podophyllotoxin to obtain compound 1-14 in compound of formula (V);

alternatively, by nucleophilic substitution reaction, 3-amino-5-mercapto-1,2,4-triazole, 3-mercapto-5-methyl-1, 2,4-triazole, 2-mercapto-5-mercapto-1,3,4-thiadiazole, 2-mercaptopyridine, 2-mercapto nicotinic acid, 2-mercapto-6-methylpyridine, 4-mercaptopyridine, 2-mercaptopyrimidine, 4-amino-2-mercaptopyrimidine, 4,6-dimethyl-2-mercaptopyrimidine, 2-mercaptobenzothiazole, 2-mercaptobenzimidazole or 2-mercaptobenzoxazole being introduced into position 4 of the C-ring of demethylepipodophyllotoxin to obtain compound 19-31 in compound of formula (V);

alternatively, the compounds of 4-S-(3-amino-1,2,4-triazole-5)-4-deoxy-podophyllotoxin (1), 4-S-(2-amino-1,3,4-thiadiazole-5)-4-deoxy-podophyllotoxin (3) or 4-S-(3-amino-1,2,4-triazole-5)-4-deoxy-4'-demethylepipodophyllotoxin (19), being subjected to sulfonamide reaction with 4-methylbenzenesulfonyl chloride or 4-methoxybenzenesulfonyl chloride, respectively, to obtain compounds 15~18 and 32~33 in compounds of formula (V);

alternatively, 4'-demethylepipodophyllotoxin is subjected to reaction with 2-amino-5-mercapto-1,3,4-thiadiazole, and product thereof being subjected to sulfonamide reaction with 4-methylbenzenesulfonyl chloride or 4-methoxybenzenesulfonyl chloride respectively, to obtain compounds 34~35 in compounds of formula (V);

The nucleophilic substitution reaction is preferably carried out under the following conditions: the podophyllotoxin or 4'-demethylepipodophyllotoxin is dissolved in trifluoroacetic acid, and then 3-amino-5-mercapto-1,2,4-triazole, 3-mercapto-5-methyl-1,2,4-triazole, 2-amino-5-mercapto-1, 3,4-thiadiazole, 2-mercapto-5-methyl-1,3,4-thiadiazole, 2-mercaptopyridine, 2-mercapto nicotinic acid, 2-mercapto-6-methylpyridine, 4-mercaptopyridine, 2-mercaptopyrimidine, 4-amino-2-mercaptopyrimidine, 4,6-dimethyl-2-mercaptopyrimidine, 2-mercaptobenzothiazole, 2-mercaptobenzimidazole or 2-mercaptobenzoxazole is added, stirred for reaction, so as to obtain product;

The sulfonamide reaction is preferably carried out as follows: product of reaction of compounds of 4-S-(3-amino-1,2,4-triazole-5)-4-deoxy-podophyllotoxin (1), 4-S-(2-amino-1,3,4-thiadiazole-5)-4-deoxy-podophyllotoxin (3) or 4-S-(3-amino-1,2,4-triazole-5)-4-deoxy-4'-demethylepipodophyllotoxin (19) or 4'-demethylepipodophyllotoxin with 2-amino-5-mercapto-1,3,4-thiadiazole is mixed with dry dichloromethane respectively, 4-methylbenzenesulfonyl chloride or 4-methoxybenzenesulfonyl chloride is then added, triethylamine is then added under ice-bath, stirred at room temperature, so as to obtain product.

In the nucleophilic substitution reaction, molar ratio between podophyllotoxin or 4'-demethylepipodophyllotoxin and 3-amino-5-mercapto-1,2,4-triazole, 3-mercapto-5-methyl-1,2,4-triazole, 2-amino-5-mercapto-1,3,4-thiadiazole, 2-mercapto-5-methyl-1,3,4-thiadiazole, 2-mercaptopyridine, 2-mercapto nicotinic acid, 2-mercapto-6-methylpyridine, 4-mercaptopyridine, 2-mercaptopyrimidine, 4-amino-2-mercaptopyrimidine, 4,6-dimethyl-2-mercaptopyrimidine, 2-mercaptobenzothiazole, 2-mercaptobenzimidazole or 2-mercaptobenzoxazole is preferably 1:1;

In the sulfonamide reaction, molar ratio between product of reaction of compounds of 4-S-(3-amino-1,2,4-triazole-5)-4-deoxy-podophyllotoxin (1), 4-S-(2-amino-1,3,4-thiadiazole-5)-4-deoxy-podophyllotoxin (3) and 4-S-(3-amino-1,2,4-triazole-5)-4-deoxy-4'-demethylepipodophyllotoxin (19) or 4'-demethylepipodophyllotoxin with 2-amino-5-mercapto-1,3,4-thiadiazole and 4-methyl-benzenesulfonyl chloride or 4-methoxybenzenesulfonyl chloride is preferably 1:2 respectively;

The stirring is such a stirring in vacuo with rotational speed of 50 to 800 rpm. Reaction temperature is −20~20° C. Reaction time is 1 to 6 hours. Preferably, rotational speed of the stirring is 600 rpm. Preferable, reaction temperature is −10~10° C. Preferred reaction time is 1 hour.

Embodiment of the present invention also provides a method for preparing crude product of, separating and purifying the sulfur-substituted podophyllotoxin derivatives, comprising:

(1) pouring crude product of Sulfur-etherification-substituted podophyllotoxin derivatives into deionized water with volume of 20~50 times thereof, then carrying out precipitation, filtration, filter-cake collection, and 45° C. drying for use;

(2) samples for separation and purification being separated, using silica gel column chromatography and gel column chromatography, sequentially, to obtain product;

(3) crude product of the sulfonamide podophyllotoxin derivatives being subjected to 35° C. drying by rotary evaporation, then separated, using silica gel column chromatography and reversed-phase column chromatography, sequentially, to obtain product;

Preferably, separation method by silica gel column chromatography comprises: (1) the silica gel column chromatography being normal or reverse phase silica gel column chromatography, wherein normal phase silica gel is mixed in organic solvent with low polarity, loaded into column, balanced with eluent which is preferably formed from chloroform and acetone with volume ratio of 40:1; reverse phase silica gel being mixed with methanol and loaded into column, balanced with eluent which is preferably formed from methanol and water with volume ratio of 60:1; (2) samples for separation and purification being dissolved with the eluent, subjected to sample adsorption, then eluted with eluent which is collected later, then the sample being evaporated to dryness and recrystallized.

Preferably, separation method by gel column chromatography comprises: (1) soaking the gel in methanol; loading processed gel into column and balanced with methanol; (2) sample preliminary separated by silica gel column chromatography being dissolved in methanol, subjected to sample absorption, and then eluated with eluent which is collected later, then the sample being evaporated to dryness and recrystallized.

In vitro BGC823, Hela, A549 cells activity inhibition tests show that the compound of formula (V) of embodiment of the invention has significantly better antitumor activity than podophyllotoxin or 4'-demethylepipodophyllotoxin. Result of the test indicates that the compound of formula (V) can be used to prepare anticancer drugs, which can be clinically applied to anti-tumor therapy.

Another purpose of embodiment of the present invention is to provide a kind of pharmaceutical composition, which is formed from combination of the compound of the formula (V) and a pharmaceutically acceptable carrier, that is, after combining of compound of the formula (V) with pharmaceutically acceptable amount and the pharmaceutically acceptable carrier, according to conventional preparing methods in the art, it can be used to preparing any kind of suitable pharmaceutical composition. Typically, the pharmaceutical composition is suitable for oral administration and injection administration, is also suitable for other methods of administration, such as transdermal administration. The pharmaceutical compositions may be in the form of tablets, capsules, powders, granules, pastilles, suppositories, or a liquid form of oral or sterile parenteral suspensions and the like. The composition may be form of large or small volume of injection, freeze-dried powder, sterile powder dispensing and the like. In order to achieve consistency of administration, the pharmaceutical composition of embodiment of the present invention is preferably in a form of single agent. Form of single agent for oral administration may be tablets and capsules, and may contain conventional excipients such as binders, e.g., syrup, acacia, gelatin, sorbitol, tragacanth, or polyvinylpyrrolidone; fillers, e.g., lactose, sugar, maize-starch, calcium phosphate, sorbitol or glycine; tabletting lubricants, e.g., magnesium stearate; disintegrants, e.g., starch, polyvinylpyrrolidone, sodium starch glycollate or microcrystalline cellulose, or a pharmaceutically acceptable wetting agents, such as sodium lauryl sulfate.

DETAILED DESCRIPTION OF THE INVENTION

Figure 1:
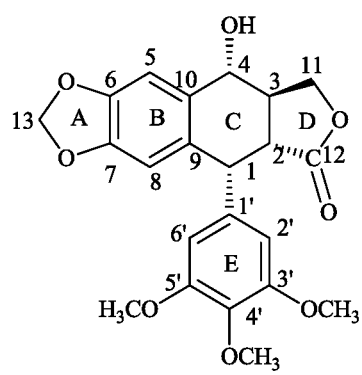
FIG. 1 shows structural formulae of podophyllotoxin and 4'-demethylepipodophyllotoxin.
Figure 1:
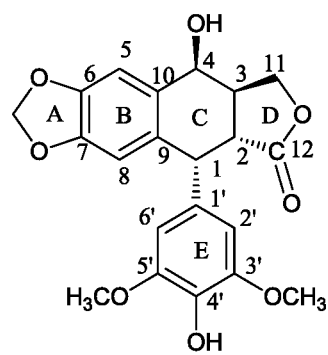
Figure 2:
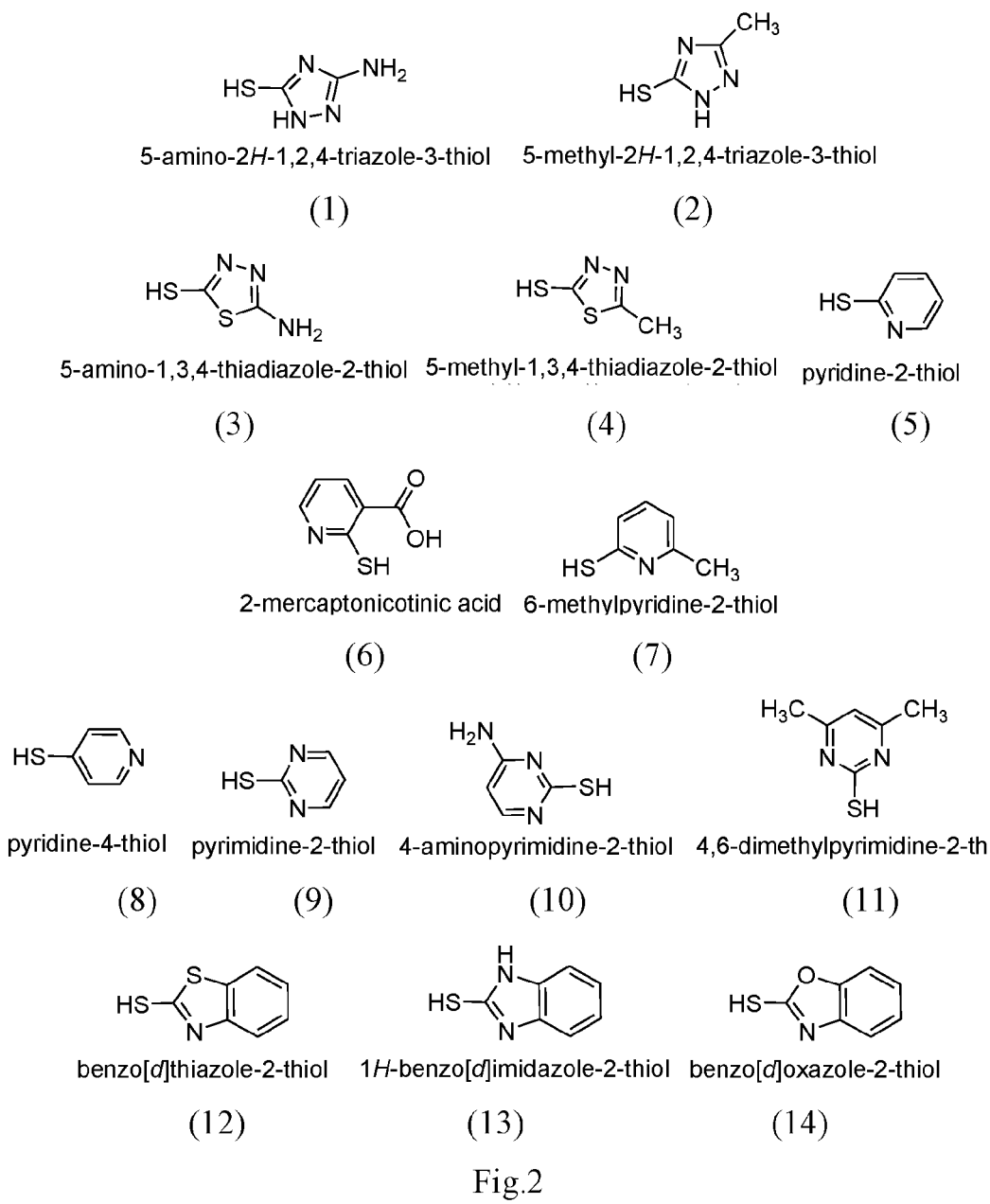
FIG. 2 shows structural formulae of 3-amino-5-mercapto-1,2,4-triazole, 3-mercapto-5-methyl-1,2,4-triazole, 2-amino-5-mercapto-1,3,4-thiadiazole, 2-mercapto-5-methyl-1,3,4-thiadiazole, 2-mercaptopyridine, 2-mercapto-nicotinic acid, 2-mercapto-6-methylpyridine, 4-mercapto-pyridine, 2-mercaptopyrimidine, 4-amino-2-mercaptopyrimidine, 4,6-dimethyl-2-mercapto-pyrimidine, 2-mercaptobenzothiazole, 2-mercaptobenzimidazole, 2-mercaptobenzothiazole.
Figure 3:
FIG. 3 shows structural formulae of 4-methylbenzenesulfonyl chloride and 4-methoxybenzene sulfonyl chloride.
Figure 4:
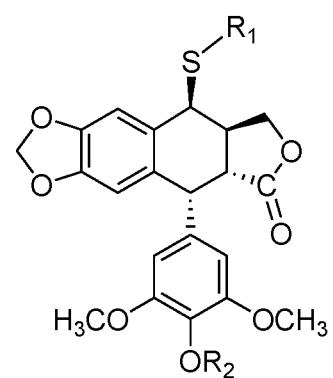
FIG. 4 shows general formulae of thiolation podophyllotoxin derivatives of embodiment of the invention.

For a fuller understanding of the nature and advantages of the present invention, reference should be made to the ensuing detailed description and the accompanying drawings. Other aspects, objects and advantages of the invention will be apparent from the drawings and the detailed description that follows. it should be noted that, the above embodiments are used to explain the technical solution of the present invention and the present invention should not be construed as being limited to such embodiments, although the present invention has been described in detail with reference to preferred embodiments thereof, it will be understood by those of ordinary skill in the art that various changes or equative replacements may be made to the technical solution of the present invention without departing from the spirit and scope of the present invention as defined by the following claims.

Test Material 1. podophyllotoxin and 4'-demethylepipodophyllotoxin: bought from Xi'an Helin Bio-technique Co., Ltd;
2. 3-amino-5-mercapto-1,2,4-triazole, 3-mercapto-5-methyl-1,2,4-triazole, 2-amino-5-mercapto-1,3,4-thiadiazole, 2-mercapto-5-methyl-1,3,4-thiadiazole, 2-mercaptopyridine, 2-mercapto nicotinic acid, 2-mercapto-6-methylpyridine, 4-mercaptopyridine, 2-mercaptopyrimidine, 4-amino-2-mercaptopyrimidine, 4,6-dimethyl-2-mercaptopyrimidine, 2-mercaptobenzothiazole, 2-mercaptobenzimidazole and 2-mercaptobenzoxazole, bought from Aladdin reagents.

Embodiment 1

Synthesis and purification of 4-S-(3-amino-1,2,4-triazole-5)-4-deoxy-podophyllotoxin (Compound (1))

(1) Synthesis of 4-S-(3-amino-1,2,4-triazole-5)-4-deoxy-podophyllotoxin taking 414 mg (1 mmol) of podophyllotoxin, 116 mg (1 mmol) of 3-amino-5-mercapto-1,2,4-triazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(3-amino-1,2,4-triazole-5)-4-deoxy-podophyllotoxin Separation and purification using silica gel column chromatography and gel column chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column. Swiss Buchi glass column C-690 with length of 460 mm and inner diameter of 15 mm) or a similar polar column separation; taking chloroform:acetone=20:1 as eluent system, with sample volume of 2 ml, constant flow rate of 1.0 ml/min; each of 2 ml of eluent as a fraction were collected. Using normal phase silica gel thin layer (Germany Merck efficient silica gel thin layer) or thin layer with similar polarity, each of fractions are viewed; taking chloroform:acetone=2:1 as a developing agent system, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=2:1 as developing solvent, fractions with Rf value of 0.5 are combined; sample of white powder from vacuum drying is 4-S-(3-amino-1,2,4-triazole-5)-4-deoxy-podophyllotoxins.

Compound (1) 4-S-(3-amino-1,2,4-triazole-5)-4-deoxy-podophyllotoxins: white powder, $C_{24}H_{24}N_4O_7S$; 513, $^1$H NMR (300 MHz, CDCl$_3$, δ): 12.154 (s, 1H) 6.998 (s, 1H), 6.420 (s, 1H), 6.295 (s, 2H), 5.939 (d, J=6.9 Hz, 2H), 5.228 (d, J=2.7 Hz, 1H), 4.883 (s, 2H), 4.560 (d, J=3.9 Hz, 1H), 4.304 (t, J=8.4 Hz, 1H), 4.070 (t, J=9.0 Hz, 1H), 3.792 (s, 3H), 3.734 (s, 6H), 3.305-3.245 (in, 2H); $^{13}$C NMR (300 MHz, CDCl$_3$, δ): 174.791, 158.148, 156.556, 152.691 (2C), 147.975, 147.262, 137.144, 136.842, 132.620, 129.658, 110.519, 110.026, 108.958 (2C), 102.074, 70.678, 60.587, 56.529 (2C), 47.837, 43.614, 41.887, 37.609

Embodiment 2

Synthesis and purification of 4-S-(5-methyl-1,2,4-triazole-3)-4-deoxy-podophyllotoxin (compound (2))

(1) Synthesis of 4-S-(5-methyl-1,2,4-triazole-3)-4-deoxy-podophyllotoxin taking 414 mg (1 mmol) of podophyllotoxin, 115 mg (1 mmol) of 3-mercapto-5-methyl-1,2,4-triazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(5-methyl-1,2,4-triazole-3)-4-deoxy-podophyllotoxins Separation and purification are carried out by silica gel column chromatography and gel column chromatography, which is same as Embodiment 1.

Compound (2) 4-S-(5-methyl-1,2,4-triazole-3)-4-deoxy-podophyllotoxins: white powder, $C_{25}H_{25}N_3O_7S$; 512, $^1$H NMR (300 MHz, CDCl$_3$, δ): 7.013 (s, 1H), 6.455 (s, 1H), 6.310 (s, 2H), 5.996 (s, 1H), 5.447 (d, J=0.9 Hz, 2H), 5.318 (s, 1H), 4.586 (s, 2H), 4.313 (t, J=2.4 Hz, 1H), 4.019 (t, J=6.9 Hz, 1H), 3.807 (s, 3H), 3.752 (s, 6H), 3.276 (s, 2H), 2.476 (s, 3H); $^{13}$C NMR (300 MHz, CDCl$_3$, δ): 174.253, 166.415, 161.623, 150.283 (2C), 148.251, 147.825, 137.203, 135.006, 133.285, 127.605, 110.287, 109.100, 108.519, 108.003, 101.569, 71.175, 61.793, 56.289 (2C), 50.275, 47.255, 44.158, 41.489, 15.178

Embodiment 3

Synthesis and purification of 4-S-(2-amino-1,3,4-thiadiazole-5)-4-deoxy-podophyllotoxin (Compound (3))

(1) Synthesis of 4-S-(2-amino-1,3,4-thiadiazole-5)-4-deoxy-podophyllotoxin taking 414 mg (1 mmol) of podophyllotoxin, 133 mg (1 mmol) of 2-amino-5-mercapto-1,3,4-thiadiazole, vacuum drying them for 1 h, taking 15 ml of trifluoroacetic acid as solvent under ice-bath condition and stirring them for 1~3 h, taking chloroform and acetone as developer, detecting end point of reaction.

Reaction system is added to deionized water of 20 to 50 times volume thereof, filter cake is collected by filtration, washed and dried to obtain crude product.

(2) Separation and purification of 4-S-(2-amino-1,3,4-thiadiazole-5)-4-deoxy-podophyllotoxin Separation and purification are carried out by silica gel column chromatography and gel column chromatography, which is same as Embodiment 1.

Compound (3) 4-S-(2-amino-1,3,4-thiadiazole-5)-4-deoxy-podophyllotoxin: white powder, $C_{24}H_{23}N_3O_7S_2$; 530, $^1$H NMR (300 MHz, CDCl$_3$, δ): 6.976 (s, 1H), 6.470 (s, 1H), 6.282 (s, 2H), 5.981 (d, J=3.0 Hz, 2H), 5.543 (d, J=3.9 Hz, 1H), 5.306 (s, 2H), 5.593 (d, J=4.8 Hz, 1H), 4.469 (t, J=8.4 Hz, 1H), 4.070 (t, J=9.3 Hz, 1H), 3.801 (s, 3H), 3.747 (s, 6H), 3.307~3.143 (in, 2H); $^{13}$C NMR (300 MHz, CDCl$_3$, δ): 177.596, 168.895, 167.893, 152.833 (2C), 148.892, 147.764, 137.786, 135.854, 132.553, 127.876, 110.366, 110.115, 108.553 (2C), 101.858, 70.897, 60.898, 56.421 (2C), 50.131, 43.925, 42.642, 37.454

Embodiment 4

Synthesis and purification of 4-S-(5-methyl-1,3,4-thiadiazol-2)-4-deoxy-podophyllotoxin (Compound (4))

(1) Synthesis of 4-S-(5-methyl-1,3,4-thiadiazol-2)-4-deoxy-podophyllotoxin taking 414 mg (1 mmol) of podophyllotoxin, 132 mg (1 mmol) of 2-mercapto-5-methyl-1,3,4-thiadiazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(5-methyl-1,3,4-thiadiazol-2)-4-deoxy-podophyllotoxin Separation and purification are carried out by silica gel column chromatography and gel column chromatography, which is same as Embodiment 1.

Compound (4) 4-S-(5-methyl-1,3,4-thiadiazol-2)-4-deoxy-podophyllotoxin: white powder, $C_{25}H_{24}N_2O_7S_2$; 529, $^1$H NMR (300 MHz, CDCl$_3$, δ): 7.233 (s, 1H), 6.548 (s, 1H), 6.367 (s, 2H), 5.997 (d, J=1.2 Hz, 2H), 5.440 (d, J=10.5 Hz, 1H), 4.624 (s, 1H), 4.322 (d, J=4.2 Hz, 1H), 4.230 (t, J=10.2 Hz, 1H), 3.806 (s, 3H), 3.771 (s, 6H), 3.057~2.891 (m, 2H), 2.761 (s, 3H); $^{13}$C NMR (300 MHz, CDCl$_3$, δ): 174.063, 166.433, 163.655, 152.903 (2C), 148.250, 147.849, 137.198, 135.136, 133.103, 127.935, 110.368, 109.180, 108.178, 108.603, 101.936, 71.742, 61.005, 56.423 (2C), 50.482, 47.790, 44.283, 41.391, 15.993

Embodiment 5

Synthesis and purification of 4-S-(pyridin-2)-4-deoxy-podophyllotoxin (compound (5))

(1) Synthesis of 4-S-(pyridin-2)-4-deoxy-podophyllotoxin taking 414 mg (1 mmol) of podophyllotoxin, 111 mg (1 mmol) of 2-mercaptopyridine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(pyridin-2)-4-deoxy-podophyllotoxin

Separation and purification are carried out by silica gel column chromatography and gel column chromatography, which is same as Embodiment 1.

Compound (5) 4-S-(pyridin-2)-4-deoxy-podophyllotoxin: white powder, $C_{27}H_{25}NO_7S$; 508, $^1H$ NMR (300 MHz, $CDCl_3$, δ): 8.443 (d, J=4.8 Hz, 2H), 6.970 (t, J=4.5 Hz, 1H), 6.871 (s, 1H), 6.369 (s, 1H), 6.255 (s, 2H), 5.846 (d, J=5.1 Hz, 2H), 5.369 (d, J=3.0 Hz, 1H), 4.523 (d, J=4.5 Hz, 1H), 4.289 (t, J=7.8 Hz, 1H), 3.762 (t, J=9.0 Hz, H), 3.697 (s, 3H), 3.662 (s, 6H), 3.212~3.177 (in, 2H); $^{13}C$ NMR (300 MHz, $CDCl_3$, δ): 174.729, 171.340 (2C), 157.728 (2C), 152.665 (2C), 148.258, 147.547, 137.143, 135.888, 132.597, 127.729, 117.702, 110.366, 110.031, 108.358, 101.789, 77.132, 70.939, 60.898, 56.338 (2C), 47.258, 43.897, 42.531, 37.189

Embodiment 6

Synthesis and purification of 4-S-(3-picolinate-2)-4-deoxy-podophyllotoxin (Compound (6))

(1) Synthesis of 4-S-(3-picolinate-2)-4-deoxy-podophyllotoxin taking 414 mg (1 mmol) of podophyllotoxin, 155 mg (1 mmol) of 2-mercapto-nicotinic acid, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(3-picolinate-2)-4-deoxy-podophyllotoxin

Separation and purification are carried out by silica gel column chromatography and gel column chromatography, which is same as Embodiment 1.

Compound (6) 4-S-(3-picolinate-2)-4-deoxy-podophyllotoxin: white powder, $C_{28}H_{25}NO_9S$; 552, $^1H$ NMR (300 MHz, $CDCl_3$, δ): 8.686 (s, 1H), 8.631 (d, J=6.6 Hz, 1H), 8.083 (s, 1H), 7.649 (s, 1H), 6.926 (s, 1H), 6.476 (s, 1H), 6.248 (s, 2H), 5.947 (s, 2H), 5.212 (s, 1H), 4.852 (s, 2H), 4.627 (d, J=4.8 Hz, 1H), 3.714 (s, 6H), 3.693 (s, 3H), 3.450 (m, 1H), 3.160~3.136 (in, 1H); $^{13}C$ NMR (300 MHz, $CDCl_3$, δ): 174.425, 161.078, 154.551, 150.555 (2C), 149.405, 148.505, 144.998, 138.422, 132.746, 126.533, 123.465, 111.080, 109.693, 108.535 (2C), 103.514 (2C), 63.167, 61.501 (2C), 57.031 (2C), 48.649, 48.419, 44.793 (2C), 32.151

Embodiment 7

Synthesis and purification of 4-S-(6-methyl-pyridin-2)-4-deoxy-podophyllotoxin (Compound (7))

(1) Synthesis of 4-S-(6-methyl-pyridin-2)-4-deoxy-podophyllotoxin taking 414 mg (1 mmol) of podophyllotoxin, 125 mg (1 mmol) of 2-mercapto-6-methylpyridine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(6-methyl-pyridin-2)-4-deoxy-podophyllotoxin Separation and purification are carried out by silica gel column chromatography and gel column chromatography, which is same as Embodiment 1.

Compound (7) 4-S-(6-methyl-pyridin-2)-4-deoxy-podophyllotoxin: white powder, $C_{28}H_{27}NO_7S$; 522, $^1H$ NMR (300 MHz, $CDCl_3$, δ): 7.418 (t, J=7.2 Hz, 1H), 6.998 (d, J=11.1 Hz, 1H), 6.961 (s, 1H), 6.915 (d, J=7.2 Hz, 1H), 6.472 (s, 1H), 6.357 (s, 2H), 5.967 (d, J=7.2 Hz, 2H), 5.529 (d, J=3.0 Hz, 1H), 4.608 (d, J=2.4 Hz, 1H), 4.358 (t, J=5.4 Hz, 1H), 3.893 (t, J=10.5 Hz, 1H), 3.817 (s, 3H), 3.780 (s, 6H), 3.309~3.267 (m, 2H), 2.508 (s, 3H); $^{13}C$ NMR (300 MHz, $CDCl_3$, δ): 175.158, 158.686, 157.138, 152.786 (2C), 148.115, 147.474, 137.516, 136.795, 136.101, 132.577, 128.947, 119.737, 118.589, 110.420, 110.099, 108.791 (2C), 101.663, 71.337, 60.978, 56.574 (2C), 46.002, 44.053, 42.692, 37.593, 24.645

Embodiment 8

Synthesis and purification of 4-S-(pyridin-4)-4-deoxy-podophyllotoxin (Compound (8))

(1) Synthesis of 4-S-(pyridin-4)-4-deoxy-podophyllotoxin taking 414 mg (1 mmol) of podophyllotoxin, 111 mg (1 mmol) of 4-mercaptopyridine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(pyridin-4)-4-deoxy-podophyllotoxin

Separation and purification are carried out by silica gel column chromatography and gel column chromatography, which is same as Embodiment 1.

Compound (8) 4-S-(pyridin-4)-4-deoxy-podophyllotoxin: white powder, $C_{27}H_{25}NO_7S$; 508, $^1H$ NMR (300 MHz, $CDCl_3$, δ): 8.465 (d, 2H), 7.142 (d, J=4.5 Hz, 2H), 6.915 (s, 1H), 6.479 (s, 1H), 6.293 (s, 2H), 5.981 (d, J=6.0 Hz, 2H), 4.994 (s, 2H), 4.598 (s, 1H), 4.282 (t, J=2.4 Hz, 1H), 4.958 (t, J=5.4 Hz, 1H), 3.793 (s, 3H), 3.746 (s, 6H), 3.303 (s, 2H); $^{13}C$ NMR (300 MHz, $CDCl_3$, δ): 174.199, 152.857 (2C), 150.066 (3C), 148.656, 147.781, 137.554, 135.476, 132.671, 127.046, 120.516 (2C), 110.275 (2C), 108.538 (2C), 101.948, 69.726, 60.984, 56.502 (2C), 46.899, 43.753, 42.224, 37.652

Embodiment 9

Synthesis and purification of 4-S-(pyrimidine-2)-4-deoxy-podophyllotoxin (Compound (9))

(1) Synthesis of 4-S-(pyrimidine-2)-4-deoxy-podophyllotoxin taking 414 mg (1 mmol) of podophyllotoxin, 112 mg (1 mmol) of 2-mercaptopyrimidine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(pyrimidine-2)-4-deoxy-podophyllotoxin

Separation and purification are carried out by silica gel column chromatography and gel column chromatography, which is same as Embodiment 1.

Compound (9) 4-S-(pyrimidine-2)-4-deoxy-podophyllotoxin: white powder, $C_{26}H_{24}N_2O_7S$; 509, $^1$H NMR (400 MHz, CDCl$_3$, δ): 8.406 (d, J=4.4 Hz, 2H), 7.537 (t, J=5.2 Hz, 1H), 6.958 (s, 1H), 6.471 (s, 1H), 6.345 (s, 2H), 5.963 (d, J=9.6 Hz, 2H), 5.593 (s, 1H), 4.596 (s, 1H), 4.355 (t, J=4.4 Hz, 1H), 3.874 (t, J=8.8 Hz, 1H), 3.817 (s, 3H), 3.768 (s, 6H), 3.316~3.218 (in, 2H); $^{13}$C NMR (400 MHz, CDCl$_3$, δ): 174.75, 158.00, 152.64 (2C), 149.28 (2C), 147.95, 147.31, 136.51, 135.70, 132.43, 128.49, 121.58, 120.45, 109.86, 108.43 (2C), 101.46, 70.96, 60.74, 56.27 (2C), 45.74, 44.21, 42.54, 37.17

Embodiment 10

Synthesis and purification of 4-S-(4-amino-pyrimidine-2)-4-deoxy-podophyllotoxin (compound (10))

(1) Synthesis of 4-S-(4-amino-pyrimidine-2)-4-deoxy-podophyllotoxin taking 414 mg (1 mmol) of podophyllotoxin, 127 mg (1 mmol) of 4-amino-2-mercaptopyrimidine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(4-amino-pyrimidine-2)-4-deoxy-podophyllotoxin Separation and purification are carried out by silica gel column chromatography and gel column chromatography, which is same as Embodiment 1.

Compound (10) 4-S-(4-amino-pyrimidine-2)-4-deoxy-podophyllotoxin: white powder, $C_{26}H_{25}N_3O_7S$; 524, $^1$H NMR (300 MHz, CDCl$_3$, δ): 8.048 (d, J=6.0 Hz, 1H), 6.976 (s, 1H), 6.461 (s, 1H), 6.334 (s, 2H), 6.209 (d, J=5.4 Hz, 1H), 5.962 (d, J=13.2 Hz, 2H), 5.399 (s, 1H), 5.028 (s, 2H), 4.585 (s, 1H), 4.375 (t, J=6.9 Hz, 1H), 3.950 (t, J=9.3 Hz, 1H), 3.808 (s, 3H), 3.763 (s, 6H), 3.242 (s, 2H); $^{13}$C NMR (300 MHz, CDCl$_3$, δ): 174.953, 170.536, 162.630, 156.102, 152.754 (2C), 148.196, 147.549, 135.985 (2C), 132.637, 128.220, 110.467, 110.101, 108.694 (2C), 101.970, 101.716, 71.105, 60.976, 59.503 (2C), 46.909, 44.011, 42.576, 37.315

Embodiment 11

Synthesis and purification of 4-S-(4,6-dimethyl-pyrimidine-2)-4-deoxy-podophyllotoxin (Compound (11))

(1) Synthesis of 4-S-(4,6-dimethyl-pyrimidine-2)-4-deoxy-podophyllotoxin taking 414 mg (1 mmol) of podophyllotoxin, 140 mg (1 mmol) of 4,6-dimethyl-2-mercaptopyrimidine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(4,6-dimethyl-pyrimidine-2)-4-deoxy-podophyllotoxin Separation and purification are carried out by silica gel column chromatography and gel column chromatography, which is same as Embodiment 1.

Compound (11) 4-S-(4,6-dimethyl-pyrimidine-2)-4-deoxy-podophyllotoxin: white powder, $C_{28}H_{28}N_2O_7S$; 537, $^1$H NMR (300 MHz, CDCl$_3$, δ): 7.196 (s, 1H), 6.775 (s, 1H), 6.528 (s, 1H), 6.377 (s, 2H), 5.964 (d, J=3.3 Hz, 2H), 5.405 (d, J=9.6 Hz, 1H), 4.621 (s, 1H), 4.345 (t, J=7.8 Hz, 1H), 4.242 (t, J=9.6 Hz, 1H), 3.795 (s, 3H), 3.764 (s, 6H), 3.016~2.912 (m, 2H), 2.421 (s, 6H); $^{13}$C NMR (300 MHz, CDCl$_3$, δ): 174.579, 170.398, 167.678 (2C), 152.846 (2C), 147.749 (2C), 135.380 (2C), 132.631, 129.453 (2C), 116.768, 110.011, 109.610, 107.806 (2C), 72.071, 61.019, 56.294 (2C), 47.848, 46.502, 44.354, 41.491, 24.110 (2C)

Embodiment 12

Synthesis and purification of 4-S-(benzothiazol-2)-4-deoxy-podophyllotoxin (Compound (12))

(1) Synthesis of 4-S-(benzothiazol-2)-4-deoxy-podophyllotoxin taking 414 mg (1 mmol) of podophyllotoxin, 167 mg (1 mmol) of 2-mercaptobenzothiazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(benzothiazol-2)-4-deoxy-podophyllotoxin

Separation and purification are carried out by silica gel column chromatography and gel column chromatography, which is same as Embodiment 1.

Compound (12) 4-S-(benzothiazol-2)-4-deoxy-podophyllotoxin: white powder, $C_{29}H_{25}NO_7S_2$; 564, $^1$H NMR (300 MHz, CDCl$_3$, δ): 7.856 (d, J=8.1 Hz, 1H), 7.792 (d, J=8.1 Hz, 1H), 7.443 (t, J=7.2 Hz, 1H), 7.333 (t, J=8.4 Hz, 1H), 6.488 (s, 1H), 6.383 (s, 1H), 6.325 (s, 2H), 5.978 (d, J=6.0 Hz, 2H), 5.766 (d, J=3.9 Hz, 1H), 4.623 (t, J=5.1 Hz, 1H), 4.464 (t, J=8.1 Hz, 1H), 3.976 (t, J=7.2 Hz, 1H), 3.805 (s, 3H), 3.766 (s, 6H), 3.356 (m, 1H), 3.234~2.172 (in, 1H); $^{13}$C NMR (300 MHz, CDCl$_3$, δ): 174.477, 165.552, 152.874 (2C), 148.690, 148.188, 147.756, 137.659, 135.525, 132.987, 128.343, 127.241, 126.558, 125.079, 121.913, 121.523, 110.254, 109.292, 108.678, 108.204, 101.872, 70.995, 60.968, 56.547 (2C), 49.922, 44.357, 42.823, 37.398

Embodiment 13

Synthesis and purification of 4-S-(benzimidazol-2)-4-deoxy-podophyllotoxin (Compound (13))

(1) Synthesis of 4-S-(benzimidazol-2)-4-deoxy-podophyllotoxin taking 414 mg (1 mmol) of podophyllotoxin, 150 mg (1 mmol) of 2-mercaptobenzimidazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(benzimidazol-2)-4-deoxy-podophyllotoxin

Separation and purification are carried out by silica gel column chromatography and gel column chromatography, which is same as Embodiment 1.

Compound (13) 4-S-(benzimidazol-2)-4-deoxy-podophyllotoxin: white powder, $C_{29}H_{26}N_2O_7S$; 547; $^1H$ NMR (400 MHz, $CDCl_3$, δ): 7.732 (d, J=6.8 Hz, 1H), 7.711 (d, J=4.0 Hz, 1H), 7.433 (t, J=7.6 Hz, 1H), 7.143 (t, J=4.4 Hz, 1H), 6.432 (s, 1H), 6.122 (s, 1H), 6.110 (s, 2H), 5.664 (d, J=6.0 Hz, 2H), 5.541 (d, J=3.2 Hz, 1H), 4.528 (t, J=5.2 Hz, 1H), 4.254 (t, J=9.6 Hz, 1H), 4.006 (t, J=5.2 Hz, 1H), 3.811 (s, 3H), 3.713 (s, 6H), 3.134~2.112 (in, 2H); $^{13}C$ NMR (400 MHz, $CDCl_3$, δ): 181.146, 176.697, 157.444 (2C), 146.645, 146.158, 145.236, 137.345, 135.634, 131.934, 127.478, 126.521, 125.445, 124.129, 120.664, 120.123, 109.184, 108.197, 107.863, 107.004, 101.652, 71.258, 61.028, 57.827 (2C), 50.961, 44.358, 41.624, 39.659

Embodiment 14

Synthesis and purification of 4-S-(benzoxazole-2)-4-deoxy-podophyllotoxin (Compound (14))

(1) Synthesis of 4-S-(benzoxazole-2)-4-deoxy-podophyllotoxin taking 414 mg (1 mmol) of podophyllotoxin, 151 mg (1 mmol) of 2-mercaptobenzimidazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(benzoxazole-2)-4-deoxy-podophyllotoxin

Separation and purification are carried out by silica gel column chromatography and gel column chromatography, which is same as Embodiment 1.

Compound (14) 4-S-(benzoxazole-2)-4-deoxy-podophyllotoxin: white powder, $C_{29}H_{25}NO_8S$; 548; $^1H$ NMR (400 MHz, $CDCl_3$, δ): 7.863 (d, J=8.4 Hz, 1H), 7.693 (d, J=6.0 Hz, 1H), 7.631 (t, J=7.2 Hz, 1H), 7.463 (t, J=8.0 Hz, 1H), 6.528 (s, 1H), 6.467 (s, 1H), 6.312 (s, 2H), 5.858 (d, J=6.8 Hz, 2H), 5.226 (d, J=3.6 Hz, 1H), 4.538 (t, J=5.2 Hz, 1H), 4.852 (t, J=8.8 Hz, 1H), 3.958 (t, J=7.6 Hz, 1H), 3.842 (s, 3H), 3.676 (s, 6H), 3.335~2.178 (in, 2H); $^{13}C$ NMR (400 MHz, $CDCl_3$, δ): 175.441, 165.557, 152.863 (2C), 148.668, 148.111, 147.743, 137.668, 135.511, 132.979, 128.325, 127.258, 126.569, 125.014, 121.916, 121.589, 109.225, 109.110, 108.678, 108.214, 101.852, 71.005, 61.084, 51.627 (2C), 50.042, 44.369, 42.816, 37.479

Embodiment 15

Synthesis and purification of 4-S-[3-N-(4-methyl-benzenesulfonamide-)-1,2,4-triazole-5-]-4-deoxy-podophyllotoxin (Compound (15))

(1) Synthesis of 4-S-[3-N-(4-methyl-benzenesulfonamide-)-1,2,4-triazole-5-]-4-deoxy-podophyllotoxin taking 515 mg (1 mmol) of 4-S-(3-amino-1,2,4-triazole-5)-4-deoxy-podophyllotoxin (Compound (1)), 382 mg (2 mmol) of 4-methylbenzene sulfonyl chloride, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product.

(2) Separation and purification of 4-S-[3-N-(4-methyl-benzenesulfonamide-)-1,2,4-triazole-5-]-4-deoxy-podophyllotoxin Separation and purification are carried out by silica gel column chromatography and gel column chromatography, which is same as Embodiment 1.

Compound (15) 4-S-[3-N-(4-methyl-benzenesulfonamide-)-1,2,4-triazole-5-]-4-deoxy-podophyllotoxin: white powder, $C_{31}H_{30}N_4O_9S_2$; 667; $^1H$ NMR (300 MHz, $CDCl_3$, δ): 7.853 (d, J=6.3 Hz, 2H), 7.398 (d, J=6.9 Hz, 2H), 6.897 (s, 1H), 6.479 (s, 1H), 6.425 (s, 1H), 6.265 (s, 2H), 5.964 (d, J=7.8 Hz, 2H), 5.183 (s, 1H), 4.531 (s, 1H), 3.807 (t, J=7.8 Hz, 1H), 3.790 (s, 3H), 3.758 (s, 6H), 3.563 (t, J=7.2 Hz, 1H), 3.107 (s, 2H), 2.450 (s, 3H); $^{13}C$ NMR (300 MHz, $CDCl_3$, δ): 174.647, 162.345 156.986, 152.807 (2C), 148.527, 147.633, 147.414, 135.652, 133.663, 132.534, 130.596 (2C), 128.136 (2C), 127.512, 110.441, 110.087, 108.588, 108.436 (2C), 101.830, 70.367, 61.015, 56.515 (2C), 47.348, 43.876, 42.376, 37.304, 22.104

Embodiment 16

Synthesis and purification of 4-S-[3-N-(4-methoxy-benzenesulfonamide-)-1,2,4-triazole-5-]-4-deoxy-podophyllotoxin (1) Synthesis of 4-S-[3-N-(4-methoxy-benzenesulfonamide-)-1,2,4-triazole-5-]-4-deoxy-podophyllotoxin taking 515 mg (1 mmol) of 4-S-(3-amino-1,2,4-triazole-5)-4-deoxy-podophyllotoxin (Compound (1)), 414 mg (2 mmol) of 4-methoxybenzene sulfonyl chloride, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product.

(2) Separation and purification of 4-S-[3-N-(4-methoxy-benzenesulfonamide-)-1,2,4-triazole-5-]-4-deoxy-podophyllotoxin Separation and purification are carried out by silica gel column chromatography and gel column chromatography, which is same as Embodiment 1.

Compound (16) 4-S-[3-N-(4-methoxy-benzenesulfonamide-)-1,2,4-triazole-5-]-4-deoxy-podophyllotoxin: white powder, $C_{31}H_{30}N_4O_{10}S_2$; 683, $^1$H NMR (300 MHz, CDCl$_3$, δ): 7.916 (d, J=8.1 Hz, 2H), 7.041 (d, J=7.8 Hz, 2H), 6.908 (s, 1H), 6.427 (s, 1H), 6.270 (s, 1H), 5.995 (s, 1H), 5.962 (d, J=7.2 Hz, 2H), 5.186 (s, 1H), 4.541 (s, 1H), 3.901 (t, J=7.2 Hz, 1H), 3.878 (s, 3H), 3.806 (s, 3H), 3.757 (s, 6H), 3.626 (t, J=4.8 Hz, 1H), 3.122 (s, 2H), 1.665 (s, 3H); $^{13}$C NMR (300 MHz, CDCl$_3$, δ): 174.585, 165.412, 156.787, 152.814 (2C), 148.528, 147.640 (2C), 137.499, 135.670, 132.533, 130.625 (2C), 127.620 (2C), 115.206 (2C), 110.475, 110.083, 108.593 (2C), 101.824, 70.436, 61.001, 56.531 (2C), 56.244, 47.436, 43.882, 42.393, 37.322

Embodiment 17

Synthesis and purification of 4-S-[2-N-(4-methyl-benzenesulfonamide-)-1,3,4-thiadiazole-5-]-4-deoxy-podophyllotoxin (Compound (17))

(1) Synthesis of 4-S-[2-N-(4-methyl-benzenesulfonamide-)-1,3,4-thiadiazole-5-]-4-deoxy-podophyllotoxin taking 530 mg (1 mmol) of 4-S-(2-amino-1,3,4-thiadiazole-5)-4-deoxy-podophyllotoxin (Compound (3)), 382 mg (2 mmol) of 4-methylbenzene sulfonyl chloride, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product.

(2) Separation and purification of 4-S-[2-N-(4-methyl-benzenesulfonamide-)-1,3,4-thiadiazole-5-]-4-deoxy-podophyllotoxin Separation and purification are carried out by silica gel column chromatography and gel column chromatography, which is same as Embodiment 1.

Compound (17) 4-S-[2-N-(4-methyl-benzenesulfonamide-)-1,3,4-thiadiazole-5-]-4-deoxy-podophyllotoxin: white powder, $C_{31}H_{29}N_3O_9S_3$; 684, $^1$H NMR (300 MHz, CDCl$_3$, δ): 8.874 (d, J=6.6 Hz, 2H), 7.453 (d, J=6.0 Hz, 2H), 6.858 (s, 1H), 6.319 (s, 1H), 6.121 (s, 1H), 6.013 (s, 2H), 5.832 (d, J=7.2 Hz, 2H), 5.111 (s, 1H), 4.521 (s, 1H), 3.782 (t, J=7.2 Hz, 1H), 3.775 (s, 3H), 3.737 (s, 6H), 3.515 (t, J=4.2 Hz, 1H), 3.257 (s, 2H), 2.360 (s, 3H); $^{13}$C NMR (300 MHz, CDCl$_3$, δ): 174.653, 161.313 155.013, 152.983 (2C), 149.372, 147.674, 147.248, 134.237, 133.238, 132.513, 130.574 (2C), 127.336 (2C), 127.014, 109.423, 109.002, 108.636, 108.126 (2C), 101.818, 70.179, 61.018, 56.423 (2C), 47.368, 43.237, 42.169, 37.125, 21.853

Embodiment 18

Synthesis and purification of 4-S-[2-N-(4-methoxy-benzenesulfonamide-)-1,3,4-thiadiazole-5-]-4-deoxy-podophyllotoxin (Compound (18))

(1) Synthesis of 4-S-[2-N-(4-methoxy-benzenesulfonamide-)-1,3,4-thiadiazole-5-]-4-deoxy-podophyllotoxin taking 530 mg (1 mmol) of 4-S-(2-amino-1,3,4-thiadiazole-5)-4-deoxy-podophyllotoxin (Compound (3)), 414 mg (2 mmol) of 4-methoxybenzene sulfonyl chloride, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product.

(2) Separation and purification of 4-S-[2-N-(4-methoxy-benzenesulfonamide-)-1,3,4-thiadiazole-5-]-4-deoxy-podophyllotoxin Separation and purification are carried out by silica gel column chromatography and gel column chromatography, which is same as Embodiment 1.

Compound (18) 4-S-[2-N-(4-methoxy-benzenesulfonamide-)-1,3,4-thiadiazole-5-]-4-deoxy-podophyllotoxin: white powder, $C_{31}H_{29}N_3O_{10}S_3$; 700, $^1$H NMR (300 MHz, CDCl$_3$, δ): 7.848 (d, J=4.2 Hz, 2H), 7.315 (d, J=6.9 Hz, 2H), 6.867 (s, 1H), 6.478 (s, 1H), 6.315 (s, 2H), 6.164 (d, J=5.2 Hz, 2H), 5.310 (s, 1H), 4.539 (s, 1H), 4.141 (t, J=9.6 Hz, 1H), 3.972 (t, J=9.3 Hz, 1H), 3.873 (s, 3H), 3.764 (s, 6H), 3.183 (s, 2H), 1.899 (s, 3H); $^{13}$C NMR (300 MHz, CDCl$_3$, δ): 174.667, 164.861, 156.766, 153.014 (2C), 149.586, 147.613 (2C), 137.602, 136.257, 131.381, 130.538 (2C), 125.616 (2C), 114.893 (2C), 109.487, 109.013, 108.604 (2C), 101.844, 69.616, 60.982, 56.135 (2C), 56.012, 47.216, 43.971, 42.643, 32.533

Embodiment 19

Synthesis and purification of 4-S-(3-amino-1,2,4-triazole-5)-4-deoxy-4'-demethylepipodophyllotoxin (Compound (19))

(1) Synthesis of 4-S-(3-amino-1,2,4-triazole-5)-4-deoxy-4'-demethylepipodophyllotoxin taking 400 mg (1 mmol) of 4'-demethylepipodophyllotoxin, 116 mg (1 mmol) of 3-amino-5-mercapto-1,2,4-triazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(3-amino-1,2, 4-triazole-5)-4-deoxy-4'-demethylepipodophyllotoxin Separation and purification are carried out by silica gel column chromatography and gel column chromatography, which is same as Embodiment 1.

Compound (19) 4-S-(3-amino-1,2,4-triazole-5)-4-deoxy-4'-demethylepipodophyllotoxin: white powder, $C_{23}H_{22}N_4O_7S$; 499; $^1H$ NMR (300 MHz, $CDCl_3$, δ): 7.041 (s, 1H) 6.420 (s, 1H), 6.315 (s, 2H), 5.926 (s, 2H), 5.224 (s, 1H), 4.539 (s, 1H), 4.297 (t, J=1.2 Hz, 1H), 4.076 (t, J=6.0 Hz, 1H), 3.710 (s, 6H), 3.302 (s, 2H); $^{13}C$ NMR (300 MHz, $CDCl_3$, δ): 175.889, 157.117, 156.325, 148.584, 147.406 (2C), 134.651, 132.793, 131.171, 128.549, 109.977, 109.463, 108.255 (2C), 101.710, 70.597, 55.563 (2C), 48.675, 43.573, 42.165, 37.820

Embodiment 20

Synthesis and purification of 4-S-(5-methyl-1,2,4-triazole-3)-4-deoxy-4'-demethylepipodophyllotoxin (Compound (20))

(1) Synthesis of 4-S-(5-methyl-1,2,4-triazole-3)-4-deoxy-4'-demethylepipodophyllotoxin taking 400 mg (1 mmol) of 4'-demethylepipodophyllotoxin, 115 mg (1 mmol) of 3-mercapto-5-methyl-1,2,4-triazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(5-methyl-1, 2,4-triazole-3)-4-deoxy-4'-demethylepipodophyllotoxin Separation and purification are carried out by silica gel column chromatography and gel column chromatography, which is same as Embodiment 1.

Compound (20) 4-S-(5-methyl-1,2,4-triazole-3)-4-deoxy-4'-demethylepipodophyllotoxin: white powder, $C_{24}H_{23}N_3O_7S$; 498; $^1H$ NMR (300 MHz, $CDCl_3$, δ): 7.015 (s, 1H) 6.461 (s, 1H), 6.318 (s, 2H), 5.974 (d, J=6.9 Hz, 2H), 5.317 (s, 1H), 4.582 (s, 1H), 4.313 (t, J=5.2 Hz, 1H), 4.005 (t, J=6.0 Hz, 1H), 3.786 (s, 6H), 3.259 (s, 2H), 2.490 (s, 3H); $^{13}C$ NMR (300 MHz, $CDCl_3$, δ): 174.569, 166.728, 165.763, 149.236, 147.682, 146.558 (2C), 134.270, 133.782, 131.048, 127.261, 109.892 (2C), 108.168 (2C), 101.914, 70.948, 56.637 (2C), 50.149, 43.582, 41.792, 37.346, 16.358

Embodiment 21

Synthesis and purification of 4-S-(5-methyl-1,3,4-thiadiazol-2)-4-deoxy-4'-demethylepipodophyllotoxin (Compound (21))

(1) Synthesis of 4-S-(5-methyl-1,3,4-thiadiazol-2)-4-deoxy-4'-demethylepipodophyllotoxin taking 400 mg (1 mmol) of 4'-demethylepipodophyllotoxin, 132 mg (1 mmol) of 2-mercapto-5-methyl-1,3,4-thiadiazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(5-methyl-1, 3,4-thiadiazol-2)-4-deoxy-4'-demethylepipodophyllotoxin Separation and purification are carried out by silica gel column chromatography and gel column chromatography, which is same as Embodiment 1.

Compound (21) 4-S-(5-methyl-1,3,4-thiadiazol-2)-4-deoxy-4'-demethylepipodophyllotoxin: white powder, $C_{24}H_{22}N_2O_7S_2$; 515; $^1H$ NMR (300 MHz, $CDCl_3$, δ): 6.946 (s, 1H) 6.477 (s, 1H), 6.292 (s, 2H), 5.981 (d, J=4.2 Hz, 2H), 5.725 (d, J=4.2 Hz, 1H), 4.598 (d, J=4.5 Hz, 1H), 4.479 (t, J=8.1 Hz, 1H), 3.902 (t, J=6.3 Hz, 1H), 3.779 (s, 6H), 3.307 (m, 1H), 3.184 (d, J=5.1 Hz, 1H), 3.138 (d, J=5.1 Hz, 1H), 2.757 (s, 3H); $^{13}C$ NMR (300 MHz, $CDCl_3$, δ): 174.550, 165.731, 164.786, 148.780, 147.721, 146.661 (2C), 134.263, 133.204, 130.798, 126.990, 110.240 (2C), 107.949 (2C), 101.936, 71.012, 56.667 (2C), 50.110, 43.753, 42.894, 37.352, 15.950

Embodiment 22

Synthesis and purification of 4-S-(pyridin-2)-4-deoxy-4'-demethylepipodophyllotoxin (Compound (22))

(1) Synthesis of 4-S-(pyridin-2)-4-deoxy-4'-demethylepipodophyllotoxin taking 400 mg (1 mmol) of 4'-demethylepipodophyllotoxin, 111 mg (1 mmol) of 2-mercaptopyridine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(pyridin-2)-4-deoxy-4'-demethylepipodophyllotoxin Separation and purification are carried out by silica gel column chromatography and gel column chromatography, which is same as Embodiment 1.

Compound (22) 4-S-(pyridin-2)-4-deoxy-4'-demethylepipodophyllotoxin: white powder, $C_{26}H_{23}NO_7S$; 494; $^1H$ NMR (300 MHz, $CDCl_3$, δ): 8.620 (d, J=5.6 Hz, 2H), 7.310 (s, 1H), 7.132 (t, J=7.5 Hz, 1H), 7.009 (s, 1H), 6.528 (s, 1H), 6.391 (s, 2H), 6.025 (d, J=8.4 Hz, 2H), 5.487 (d, J=7.5 Hz, 1H), 4.663 (d, J=7.2 Hz, 1H), 4.424 (t, J=5.1 Hz, 1H), 3.910 (t, J=9.0 Hz, 1H), 3.846 (s, 6H), 3.369 (m, 1H), 3.313 (d, J=4.2 Hz, 1H), 3.267 (d, J=4.2 Hz, 1H); $^{13}C$ NMR (300 MHz, $CDCl_3$, δ): 174.772, 171.707, 157.715 (2C), 148.349, 147.611, 146.674 (2C), 134.356, 132.937, 131.348, 127.828, 117.611, 110.345 (2C), 110.023, 108.330 (2C), 101.745, 70.922, 56.731 (2C), 47.393, 43.845, 42.767, 37.204

Embodiment 23

Synthesis and purification of 4-S-(3-picolinate-2)-deoxy-4'-demethylepipodophyllotoxin (Compound (23))

(1) Synthesis of 4-S-(3-picolinate-2)-deoxy-4'-demethylepipodophyllotoxin taking 400 mg (1 mmol) of 4'-demethylepipodophyllotoxin, 155 mg (1 mmol) of 2-mercapto-nicotinic acid, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(3-picolinate-2)-deoxy-4'-demethylepipodophyllotoxin Separation and purification are carried out by silica gel column chromatography and gel column chromatography, which is same as Embodiment 1.

Compound (23) 4-S-(3-picolinate-2)-deoxy-4'-demethylepipodophyllotoxin: white powder, $C_{27}H_{23}NO_9S$; 538, $^1H$ NMR (300 MHz, CDCl$_3$, δ): 8.588 (d, J=9.6 Hz, 1H), 8.538 (d, J=7.2 Hz, 1H), 7.610 (t, J=6.3 Hz, 1H), 6.910 (s, 1H), 6.476 (s, 1H), 6.226 (s, 2H), 5.957 (d, J=4.2 Hz, 2H), 5.187 (d, J=6.3 Hz, 2H), 4.953 (s, 6H), 4.821 (s, 1H), 3.429 (m, 1H), 3.103 (d, J=4.2 Hz, 1H), 3.080 (d, J=4.2 Hz, 1H); $^{13}C$ NMR (300 MHz, CDCl$_3$, δ): 173.243, 167.585, 158.906, 148.913, 147.714 (2C), 146.236, 142.735, 134.765, 131.536, 125.051, 121.948, 109.480, 108.071, 106.767 (2C), 101.858, 61.407, 55.487 (2C), 46.972, 46.624, 43.304, 30.495

Embodiment 24

Synthesis and purification of 4-S-(6-methyl-pyridin-2)-4-deoxy-4'-demethylepipodophyllotoxin (Compound (24))

(1) Synthesis of 4-S-(6-methyl-pyridin-2)-4-deoxy-4'-demethylepipodophyllotoxin taking 414 mg (1 mmol) of 4'-demethylepipodophyllotoxin, 125 mg (1 mmol) of 2-mercapto-6-methylpyridine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(6-methyl-pyridin-2)-4-deoxy-4'-demethylepipodophyllotoxin Separation and purification are carried out by silica gel column chromatography and gel column chromatography, which is same as Embodiment 1.

Compound (24) 4-S-(6-methyl-pyridin-2)-4-deoxy-4'-demethylepipodophyllotoxin: white powder, $C_{27}H_{25}NO_7S$; 508, $^1H$ NMR (300 MHz, CDCl$_3$, δ): 7.414 (d, J=7.5 Hz, 1H), 6.996 (d, J=11.4 Hz, 1H), 6.958 (s, 1H), 6.914 (d, J=7.2 Hz, 1H), 6.469 (s, 1H), 6.367 (s, 2H), 5.968 (d, J=9.3 Hz, 2H), 5.521 (s, 1H), 5.440 (s, 1H), 4.594 (s, 1H), 4.346 (t, J=8.1 Hz, 1H), 3.888 (t, J=9.3 Hz, 1H), 3.810 (s, 6H), 3.253 (m, 2H), 2.508 (s, 3H); $^{13}C$ NMR (300 MHz, CDCl$_3$, δ): 174.953, 158.410, 156.890, 147.831 (2C), 147.170, 146.368, 136.520, 134.059, 132.497, 131.329, 128.685, 119.442, 118.317, 110.101, 109.834, 108.146 (2C), 101.393, 71.049, 56.517 (2C), 45.728, 43.617, 42.548, 37.273, 24.401

Embodiment 25

Synthesis and purification of 4-S-(pyridin-4)-4-deoxy-4'-demethylepipodophyllotoxin (Compound (25))

(1) Synthesis of 4-S-(pyridin-4)-4-deoxy-4'-demethylepipodophyllotoxin taking 400 mg (1 mmol) of 4'-demethylepipodophyllotoxin, 111 mg (1 mmol) of 4-mercaptopyridine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(pyridin-4)-4-deoxy-4'-demethylepipodophyllotoxin Separation and purification are carried out by silica gel column chromatography and gel column chromatography, which is same as Embodiment 1.

Compound (25) 4-S-(pyridin-4)-4-deoxy-4'-demethylepipodophyllotoxin: white powder, $C_{26}H_{23}NO_7S$; 494, $^1H$ NMR (300 MHz, CDCl$_3$, δ): 8.464 (s, 2H), 7.148 (d, J=6.9 Hz, 2H), 6.912 (s, 1H), 6.480 (s, 1H), 6.305 (s, 1H), 5.983 (d, J=7.2 Hz, 1H), 4.994 (s, 1H), 4.590 (s, 1H), 4.267 (t, J=6.0 Hz, 1H), 3.939 (t, J=10.2 Hz, 1H), 3.775 (s, 6H), 3.289 (s, 2H); $^{13}C$ NMR (300 MHz, CDCl$_3$, δ): 174.278, 149.898 (2C), 148.857, 148.674, 147.746, 146.789 (2C), 134.550, 132.890, 130.865, 126.996, 120.539 (2C), 110.326, 110.157, 108.258 (2C), 101.942, 69.712, 56.742 (2C), 46.951, 43.589, 42.351, 37.582

Embodiment 26

Synthesis and purification of 4-S-(pyrimidine-2)-4-deoxy-4'-demethylepipodophyllotoxin (Compound (26))

(1) Synthesis of 4-S-(pyrimidine-2)-4-deoxy-4'-demethylepipodophyllotoxin taking 400 mg (1 mmol) of 4'-demethylepipodophyllotoxin, 112 mg (1 mmol) of 2-mercaptopyrimidine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(pyrimidine-2)-4-deoxy-4'-demethylepipodophyllotoxin Separation and purification are carried out by silica gel column chromatography and gel column chromatography, which is same as Embodiment 1.

Compound (26) 4-S-(pyrimidine-2)-4-deoxy-4'-demethylepipodophyllotoxin: white powder, $C_{25}H_{22}N_2O_7S$; 495, $^1$H NMR (300 MHz, CDCl$_3$, δ): 8.468 (d, J=7.2 Hz, 1H), 7.599 (t, J=6.9 Hz, 1H), 7.253 (d, J=7.8 Hz, 1H), 7.122 (t, J=6.0 Hz, 1H), 6.998 (s, 1H), 6.512 (s, 1H), 6.388 (s, 2H), 6.009 (d, J=7.2 Hz, 2H), 5.643 (t, J=6.0 Hz, 1H), 4.645 (d, J=4.2 Hz, 1H), 4.391 (t, J=8.1 Hz, 1H), 3.897 (t, J=9.0 Hz, 1H), 3.837 (s, 6H), 3.359~3.240 (in, 2H); $^{13}$C NMR (300 MHz, CDCl$_3$, δ): 175.170, 158.169, 149.399, 148.178, 147.469, 146.617, 136.854, 134.157, 132.823, 131.404, 128.566, 121.896, 120.562, 110.316, 110.118, 108.131 (2C), 101.717, 71.234, 56.674 (2C), 46.031, 43.845, 42.852, 37.317

Embodiment 27

Synthesis and purification of 4-S-(4-amino-pyrimidine-2)-4-deoxy-4'-demethylepipodophyllotoxin (Compound (27))

(1) Synthesis of 4-S-(4-amino-pyrimidine-2)-4-deoxy-4'-demethylepipodophyllotoxin taking 400 mg (1 mmol) of 4'-demethylepipodophyllotoxin, 127 mg (1 mmol) of 4-amino-2-mercaptopyrimidine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(4-amino-pyrimidine-2)-4-deoxy-4'-demethylepipodophyllotoxin Separation and purification are carried out by silica gel column chromatography and gel column chromatography, which is same as Embodiment 1.

Compound (27) 4-S-(4-amino-pyrimidine-2)-4-deoxy-4'-demethylepipodophyllotoxin: white powder, $C_{25}H_{23}N_3O_7S$; 510, $^1$H NMR (300 MHz, CDCl$_3$, δ): 7.873 (d, J=5.4 Hz, 1H), 6.929 (s, 1H), 6.416 (s, 1H), 6.308 (s, 2H), 6.229 (d, J=6.0 Hz, 1H), 5.923 (d, J=2.1 Hz, 2H), 5.398 (d, J=3.0 Hz, 2H), 4.542 (d, J=3.9 Hz, 2H), 4.418 (t, J=4.5 Hz, 1H), 3.916 (t, J=8.1 Hz, 1H) 3.732 (s, 6H), 3.341~3.235 (in, 2H); $^{13}$C NMR (300 MHz, CDCl$_3$, δ): 176.106, 169.748, 163.635, 154.857, 148.217, 147.507, 147.296 (2C), 134.600, 132.778, 131.118, 128.072, 110.171, 109.791, 108.321 (2C), 101.773, 101.667, 71.450, 56.095 (2C), 46.031, 43.845, 42.852, 37.317

Embodiment 28

Synthesis and purification of 4-S-(4,6-dimethyl-pyrimidine-2)-4-deoxy-4'-demethylepipodophyllotoxin (Compound (28))

(1) Synthesis of 4-S-(4,6-dimethyl-pyrimidine-2)-4-deoxy-4'-demethylepipodophyllotoxin taking 400 mg (1 mmol) of 4'-demethylepipodophyllotoxin, 140 mg (1 mmol) of 4,6-dimethyl-2-mercaptopyrimidine, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(4,6-dimethyl-pyrimidine-2)-4-deoxy-4'-demethylepipodophyllotoxin Separation and purification are carried out by silica gel column chromatography and gel column chromatography, which is same as Embodiment 1.

Compound (28) 4-S-(4,6-dimethyl-pyrimidine-2)-4-deoxy-4'-demethylepipodophyllotoxin: white powder, $C_{27}H_{26}N_2O_7S$; 523, $^1$H NMR (300 MHz, CDCl$_3$, δ): 7.209 (s, 1H), 6.783 (d, J=0.9 Hz, 1H), 6.540 (s, 1H), 6.400 (s, 2H), 5.954 (s, 2H), 5.383 (s, 2H), 4.623 (s, 1H), 4.324~4.251 (m, 2H), 3.802 (s, 6H), 2.958 (s, 2H), 2.432 (s, 6H); $^{13}$C NMR (300 MHz, CDCl$_3$, δ): 174.611, 170.426, 167.669 (2C), 147.421, 147.580, 146.736 (2C), 133.906, 132.809, 130.840, 129.489, 116.758, 110.005, 109.569, 107.572 (2C), 101.720, 72.037, 56.520 (2C), 47.939, 46.490, 44.155, 41.411, 24.080 (2C)

Embodiment 29

Synthesis and purification of 4-S-(benzothiazol-2)-4-deoxy-4'-demethylepipodophyllotoxin (Compound (29))

(1) Synthesis of 4-S-(benzothiazol-2)-4-deoxy-4'-demethylepipodophyllotoxin taking 400 mg (1 mmol) of 4'-demethylepipodophyllotoxin, 167 mg (1 mmol) of 2-mercaptobenzothiazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(benzothiazol-2)-4-deoxy-4'-demethylepipodophyllotoxin Separation and purification are carried out by silica gel column chromatography and gel column chromatography, which is same as Embodiment 1.

Compound (29) 4-S-(benzothiazol-2)-4-deoxy-4'-demethylepipodophyllotoxin: white powder, $C_{28}H_{23}NO_7S_2$; 550, $^1$H NMR (400 MHz, CDCl$_3$, δ): 7.86 (d, J=0.8 Hz, 1H), 7.79 (d, J=0.8 Hz, 1H), 7.44 (t, J=0.8 Hz, 1H), 7.33 (t, J=0.8 Hz, 1H), 7.00 (s, 1H), 6.49 (s, 1H), 6.34 (s, 2H), 5.98 (d, J=1.2 Hz, 2H), 5.76 (d, J=0.4 Hz, 1H), 5.28 (s, 1H), 4.61 (d, J=0.4 Hz, 1H), 4.44 (t, J=0.8 Hz, 1H), 3.97 (t, J=0.8 Hz, 1H), 3.79 (s, 6H), 3.36 (m, 1H), 3.21~3.17 (in, 1H); $^{13}$C NMR (400 MHz, CDCl$_3$, δ): 172.88, 163.25, 151.35 (2C), 148.69, 148.38, 147.52, 136.43, 134.43, 133.01, 127.36, 126.37, 125.551, 125.13, 122.15, 121.33, 109.98, 109.15, 108.57, 108.20, 101.97, 71.00, 55.57 (2C), 50.01, 42.14, 41.92, 34.57

Embodiment 30

Synthesis and purification of 4-S-(benzimidazole-2)-4-deoxy-4'-demethylepipodophyllotoxin (Compound (30))

(1) Synthesis of 4-S-(benzimidazole-2)-4-deoxy-4'-demethylepipodophyllotoxin taking 400 mg (1 mmol) of 4'-demethylepipodophyllotoxin, 150 mg (1 mmol) of 2-mercaptobenzimidazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(benzimidazole-2)-4-deoxy-4'-demethylepipodophyllotoxin Separation and purification are carried out by silica gel column chromatography and gel column chromatography, which is same as Embodiment 1.

Compound (30) 4-S-(benzimidazole-2)-4-deoxy-4'-demethylepipodophyllotoxin: white powder, $C_{28}H_{24}N_2O_7S$; 533, $^1$H NMR (400 MHz, CDCl$_3$, δ): 8.12 (d, J=1.6 Hz, 1H), 7.85 (d, J=3.6 Hz, 1H), 7.41 (t, J=0.8 Hz, 1H), 7.31 (t, J=0.8 Hz, 1H), 7.02 (s, 1H), 6.44 (s, 1H), 6.35 (s, 2H), 6.13 (d, J=0.8 Hz, 2H), 5.75 (d, J=0.4 Hz, 1H), 5.32 (s, 1H), 4.78 (d, J=0.4 Hz, 1H), 4.35 (t, J=0.8 Hz, 1H), 4.17 (t, J=0.8 Hz, 1H), 3.82 (s, 6H), 3.63 (m, 1H), 3.23~3.19 (in, 1H); $^{13}$C NMR (400 MHz, CDCl$_3$, δ): 175.82, 164.73, 150.53 (2C), 147.96, 147.31, 147.02, 136.55, 134.36, 132.98, 127.03, 126.55, 125.48, 125.01, 122.00, 121.34, 110.98, 110.15, 109.59, 108.15, 102.04, 70.90, 56.48 (2C), 49.51, 41.99, 41.15, 37.63

Embodiment 31

Synthesis and purification of 4-S-(benzoxazole-2)-4-deoxy-4'-demethylepipodophyllotoxin (Compound (31))

(1) Synthesis of 4-S-(benzoxazole-2)-4-deoxy-4'-demethylepipodophyllotoxin taking 400 mg (1 mmol) of 4'-demethylepipodophyllotoxin, 151 mg (1 mmol) of 2-mercaptobenzoxazole, vacuum drying them for 1 h, taking 15 ml of trifluoroacetic acid as solvent under ice-bath condition and stirring them for 1~3 h, taking chloroform and acetone as developer, detecting end point of reaction. Reaction system is added to deionized water of 20 to 50 times volume thereof, filter cake is collected by filtration, washed and dried to obtain crude product.

(2) Separation and purification of 4-S-(benzoxazole-2)-4-deoxy-4'-demethylepipodophyllotoxin Separation and purification are carried out by silica gel column chromatography and gel column chromatography, which is same as Embodiment 1.

Compound (31) 4-S-(benzoxazole-2)-4-deoxy-4'-demethylepipodophyllotoxin: white powder, $C_{28}H_{23}NO_8S$; 534, $^1$H NMR (400 MHz, CDCl$_3$, δ): 7.53 (d, J=0.6 Hz, 1H), 7.25 (d, J=1.6 Hz, 1H), 7.16 (t, J=0.4 Hz, 1H), 7.01 (t, J=0.4 Hz, 1H), 6.97 (s, 1H), 6.44 (s, 1H), 6.28 (s, 2H), 6.06 (d, J=0.4 Hz, 2H), 5.82 (d, J=0.4 Hz, 1H), 5.26 (s, 1H), 4.87 (d, J=0.4 Hz, 1H), 4.26 (t, J=0.4 Hz, 1H), 4.03 (t, J=0.8 Hz, 1H), 3.96 (s, 6H), 3.78 (m, 1H), 3.55~3.38 (in, 1H); $^{13}$C NMR (400 MHz, CDCl$_3$, δ): 178.64, 168.59, 155.92 (2C), 148.23, 147.69, 146.50, 137.44, 135.28, 133.27, 128.03, 127.15, 125.49, 125.06, 121.93, 120.44, 111.10, 110.14, 109.69, 108.92, 101.94, 71.18, 55.66 (2C), 48.33, 42.17, 41.29, 36.55

Embodiment 32

Synthesis and purification of 4-S-[3-N-(4-methyl-benzenesulfonamide-)-1,2,4-triazole-5-]-4-deoxy-4'-demethylepipodophyllotoxin (Compound (32))

(1) Synthesis of 4-S-[3-N-(4-methyl-benzenesulfonamide-)-1,2,4-triazole-5-]-4-deoxy-4'-demethylepipodophyllotoxin taking 501 mg (1 mmol) of 4-S-(3-amino-1,2,4-triazole-5)-4-deoxy-4'-demethylepipodophyllotoxin (Compound (19)), 382 mg (2 mmol) of 4-methylbenzene sulfonyl chloride, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product.

(2) Separation and purification of 4-S-[3-N-(4-methyl-benzenesulfonamide-)-1,2,4-triazole-5-]-4-deoxy-4'-demethylepipodophyllotoxin Separation and purification are carried out by silica gel column chromatography and gel column chromatography, which is same as Embodiment 1.

Compound (32) 4-S-[3-N-(4-methyl-benzenesulfonamide-)-1,2,4-triazole-5-]-4-deoxy-4'-demethylepipodophyllotoxin: white powder, $C_{30}H_{28}N_4O_9S_2$; 653, $^1$H NMR (300 MHz, CDCl$_3$, δ): 8.270 (s, 2H), 7.891 (d, J=7.8 Hz, 2H), 7.523 (t, J=7.5 Hz, 2H), 6.941 (s, 1H), 6.442 (s, 1H), 6.223 (s, 2H), 6.011 (d, J=7.5 Hz, 2H), 5.170 (s, 1H), 4.467 (d, J=5.1 Hz, 1H), 3.935 (t, J=6.6 Hz, 1H), 3.444 (t, J=8.7 Hz, 1H), 3.332 (s, 6H), 3.166 (m, 2H), 2.403 (s, 3H); $^{13}$C NMR (300 MHz, CDCl$_3$, δ): 174.573, 162.728, 158.578 (2C), 148.168, 147.830, 147.239 (2C), 144.325, 139.520, 135.479, 133.903, 133.298, 131.146 (2C), 128.234 (2C), 110.258, 110.129, 109.229 (2C), 102.110, 70.163, 56.742 (2C), 47.275, 43.336, 41.971, 37.287, 21.897

Embodiment 33

Synthesis and purification of 4-S-[3-N-(4-methoxy-benzenesulfonamide-)-1,2,4-triazole-5-]-4-deoxy-4'-demethylepipodophyllotoxin (Compound (33))

(1) Synthesis of 4-S-[3-N-(4-methoxy-benzenesulfonamide-)-1,2,4-triazole-S-]-4-deoxy-4'-demethylepipodophyllotoxin taking 501 mg (1 mmol) of 4-S-(3-amino-1,2,4-triazole-5)-4-deoxy-4'-demethylepipodophyllotoxin (Compound (19)), 414 mg (2 mmol) of 4-methoxybenzene sulfonyl chloride, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product.

(2) Separation and purification of 4-S-[3-N-(4-methoxy-benzenesulfonamide-)-1,2,4-triazole-5-]-4-deoxy-4'-demethylepipodophyllotoxin Separation and purification are carried out by silica gel column chromatography and gel column chromatography, which is same as Embodiment 1.

Compound (33) 4-S-[3-N-(4-methoxy-benzenesulfonamide-)-1,2,4-triazole-5-]-4-deoxy-4'-demethylepipodophyllotoxin: white powder, $C_{30}H_{28}N_4O_{10}S_2$; 669, $^1$H NMR (300 MHz, CDCl$_3$, δ): 7.920 (d, J=5.4 Hz, 2H), 7.047 (d, J=8.7 Hz, 2H), 6.912 (s, 1H), 6.432 (s, 1H), 6.286 (s, 2H), 5.967 (d, J=7.5 Hz, 2H), 5.907 (s, 1H), 5.188 (s, 1H), 4.526 (s, 1H), 3.885 (s, 4H), 3.797 (s, 6H), 3.607 (t, J=4.2 Hz, 1H), 3.103 (d, J=0.6 Hz, 2H), 1.624 (s, 3H); $^{13}$C NMR (300 MHz, CDCl$_3$, δ): 174.638, 165.339, 162.118, 156.828, 148.444, 147.529, 146.601 (2C), 137.654, 134.221, 132.646, 131.098, 130.522 (2C), 127.511, 115.146 (2C), 110.348, 110.025, 108.126 (2C), 101.753, 70.354, 56.666 (2C), 56.188, 47.297, 43.654, 42.444, 37.182

Embodiment 34

Synthesis and purification of 4-S-[2-N-(4-methyl-benzenesulfonamide-)-1,3,4-thiadiazole-5-]-4-deoxy-4'-demethylepipodophyllotoxin (Compound (34))

(1) Synthesis of 4-S-[2-N-(4-methyl-benzenesulfonamide-)-1,3,4-thiadiazole-5-]-4-deoxy-4'-demethyl-epipodophyllotoxin taking 400 mg (1 mmol) of 4'-demethylepipodophyllotoxin, 133 mg (1 mmol) of 2-amino-5-mercapto-1,3,4-thiadiazole, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product. Taking the crude product as substrate, 382 mg (2 mmol) of 4-methylbenzene sulfonyl chloride is then added, by taking 15 ml of methylene chloride as solvent under ice-bath condition and stirring them for 15 min, then adding 0.5 ml of triethylamine, stirring them for reaction for 1 h, taking chloroform and acetone as developer, end point of reaction is detected. Reaction system is subjected to rotary evaporation at 35° C., and dried to obtain crude product (2) Separation and purification of 4-S-[2-N-(4-methyl-benzenesulfonamide-)-1,3,4-thiadiazole-5-]-4-deoxy-4'-demethylepipodophyllotoxin Separation and purification are carried out by silica gel column chromatography and gel column chromatography, which is same as Embodiment 1.

Compound (34) 4-S-[2-N-(4-methyl-benzenesulfonamide-)-1,3,4-thiadiazole-5-]-4-deoxy-4'-demethylepipodophyllotoxin: white powder, $C_{30}H_{27}N_3O_9S_3$; 670, $^1$H NMR (400 MHz, CDCl$_3$, δ): 7.826 (d, J=5.6 Hz, 2H), 7.330 (d, J=5.6 Hz, 2H), 6.971 (s, 1H), 6.439 (s, 1H), 6.273 (s, 2H), 5.981 (d, J=6.8 Hz, 2H), 5.783 (s, 1H), 5.466 (s, 1H), 4.577 (d, J=2.0 Hz, 1H), 4.446 (t, J=4.0 Hz, 1H), 4.104 (t, J=6.8 Hz, 1H), 3.550 (s, 6H), 3.233 (d, J=7.2 Hz, 2H), 2.447 (s, 3H); $^{13}$C NMR (400 MHz, CDCl$_3$, δ): 174.141, 168.755, 152.762, 152.435 (2C), 148.324, 147.452, 144.519 (2C), 139.207, 134.414, 131.795, 129.045, 128.152 (2C), 127.070 (2C), 110.097, 109.731, 107.535 (2C), 101.616, 70.596, 55.861, 55.841, 49.626, 43.557, 42.098, 37.096, 21.503

Embodiment 35

Synthesis and purification of 4-S-[2-N-(4-methoxy-benzenesulfonamide-)-1,3,4-thiadiazole-5-]-4-deoxy-4'-demethylepipodophyllotoxin (Compound (35))

(1) Synthesis of 4-S-[2-N-(4-methoxy-benzenesulfonamide-)-1,3,4-thiadiazole-5-]-4-deoxy-4'-demethylepipodophyllotoxin taking 400 mg (1 mmol) of 4'-demethylepipodophyllotoxin, 133 mg (1 mmol) of 2-amino-5-mercapto-1,3,4-thiadiazole, vacuum drying them for 1 h, taking 15 ml of methylene chloride as solvent under ice-bath condition and stirring them for 15 min, then adding 0.5 ml of triethylamine, stirring them for reaction for 1 h, taking chloroform and acetone as developer, detecting end point of reaction. Reaction system is subjected to rotary evaporation at 35° C., and dried to obtain crude product. Taking the crude product as substrate, 414 mg (2 mmol) of 4-methoxybenzene sulfonyl chloride is then added, by taking 15 ml of methylene chloride as solvent under ice-bath condition and stirring them for 15 min, then adding 0.5 ml of triethylamine, stirring them for reaction for 1 h, taking chloroform and acetone as developer, end point of reaction is detected. Reaction system is subjected to rotary evaporation at 35° C., and dried to obtain crude product (2) Separation and purification of 4-S-[2-N-(4-methoxy-benzenesulfonamide-)-1,3,4-thiadiazole-5-]-4-deoxy-4'-demethylepipodophyllotoxin Separation and purification are carried out by silica gel column chromatography and gel column chromatography, which is same as Embodiment 1.

Compound (35) 4-S-[2-N-(4-methoxy-benzenesulfonamide-)-1,3,4-thiadiazole-5-]-4-deoxy-4'-demethylepipodophyllotoxin: white powder, $C_{30}H_{27}N_3O_{10}S_3$; 686, $^1$H NMR (300 MHz, CDCl$_3$, δ): 7.900 (d, J=8.4 Hz, 2H), 6.984 (s, 3H), 6.464 (s, 1H), 6.273 (s, 2H), 5.996 (d, J=3.0 Hz, 2H), 5.520 (s, 1H), 5.586 (s, 1H), 4.476 (t, J=6.3 Hz, 1H), 4.093 (t, J=8.7 Hz, 1H), 3.893 (s, 3H), 3.581 (s, 6H), 3.208 (s, 2H); $^{13}$C NMR (300 MHz, CDCl$_3$, δ): 174.557, 169.070, 164.009, 152.949 (2C), 148.769, 147.916, 139.557, 132.250, 130.857 (2C), 129.265, 127.588 (2C), 127.502, 114.025 (2C), 110.528, 110.187, 108.026 (2C), 102.027, 71.008, 56.365 (2C), 55.996, 50.082, 43.997, 42.547, 37.543

Experiment 1

Test of compounds of embodiment of the present invention on inhibiting tumor cell activity
1) Test Materials
1, compounds for the test: the compounds prepared in embodiments 1 to 35, noted with compounds (1) to (35);

2, compounds for comparison: podophyllotoxin and 4'-demethylepipodophyllotoxins, which are available from Xi'an Helin Bio-technique Co., Ltd., with 98% purity; and etoposide;

3, cell lines: A549, BGC823, Hela cell line and normal human hepatocytes which are available from Wu Han boster Co., Ltd.;

2) Test Method

A549, BGC823, Hela cell line and normal human hepatocytes in logarithmic growth phase are subjected to 1000 rpm centrifugation for 5 min, supernatant is then discarded, moderate medium is suspended, the cell concentration is adjusted to $3.5 \times 10^4$/well, the cells were seeded in 96-wells culture plate, and following experimental groups are set:

a negative control group; 35 test groups with same concentration (ie: groups of Compound (1) to Compound (35)); three control groups: groups of podophyllotoxin, 4'-demethylepipodophyllotoxin and etoposide.

Taking RPMI1640 containing 10% of calf serum as nutrient solution, 0.10 mL of cells per well is incubated under conditions of 37° C., 5% CO2 and saturated humidity for 24 h to nearly be covered, then the nutrient solution is discarded. For the 35 test groups, 0.10 M of nutrient solution of RPMI1640 with 10% calf serum containing same amount of the compound (1) to compound (35) is added respectively; for groups of podophyllotoxin, 4'-demethylepipodophyllotoxin and etoposide, 0.10 M of nutrient solution of RPMI1640 with 10% calf serum is added containing podophyllotoxin, 4'-demethylepipodophyllotoxin and etoposide, respectively; amount of podophyllotoxin, 4'-demethylepipodophyllotoxin or etoposide is same as the amount of the compounds (1) to (35); for the negative control group, DMSO with a final concentration of 0.5% is added; for each group, three complex wells are set, cultivation is continued for 48 h, 10 μl of MTT with 5 mg/ml is added to each well, then put at 37° C. for 4 h. 100 μl of DMSO is added to each well, then vibrated at 37° C. by shaker table for 30 min, then measuring absorbance (OD) at 492 nm, calculating MTT ratio=OD value of drug group/OD value of the negative control group.

3) Test Results

Test results are shown in Table 1. From Table 1, anti-tumor activity of the compounds (1) to (35) to the Hela cell line is much better than those of the groups of podophyllotoxin, 4'-demethylepipodophyllotoxins and podophyllotoxin-type derivatives and etoposide which are available from market as antitumor drugs.

TABLE 1

IC$_{50}$ values of Sulfur substituted podophyllotoxin-type derivatives to in vitro tumor cell lines and normal cell lines

| compound | IC$_{50}$ (μM) | | |
|---|---|---|---|
| | Hela | BGC823 | A549 |
| 1 | 2.86 ± 0.34 | 0.83 ± 0.14 | 5.76 ± 0.34 |
| 2 | 0.15 ± 0.03 | 0.27 ± 0.03 | 1.01 ± 0.28 |
| 3 | 0.06 ± 0.01 | 0.71 ± 0.03 | 1.98 ± 2.54 |
| 4 | 2.18 ± 0.07 | 4.01 ± 0.02 | 4.11 ± 0.93 |
| 5 | 0.73 ± 0.05 | 4.76 ± 0.12 | 5.66 ± 0.47 |
| 6 | 1.71 ± 0.07 | 2.65 ± 0.53 | 0.83 ± 0.25 |
| 7 | 0.90 ± 0.05 | 3.51 ± 0.14 | 1.12 ± 0.28 |
| 8 | 3.85 ± 0.14 | 1.52 ± 0.11 | 8.12 ± 0.09 |
| 9 | 3.64 ± 0.46 | 0.71 ± 0.14 | 6.40 ± 0.38 |
| 10 | 1.85 ± 0.12 | 1.32 ± 0.15 | 4.65 ± 0.26 |
| 11 | 0.11 ± 0.01 | 1.99 ± 0.34 | 3.31 ± 0.26 |
| 12 | 0.60 ± 0.39 | 0.31 ± 0.34 | 3.85 ± 0.47 |
| 13 | 3.10 ± 0.16 | 2.32 ± 0.01 | 6.76 ± 4.31 |

TABLE 1-continued

IC$_{50}$ values of Sulfur substituted podophyllotoxin-type derivatives to in vitro tumor cell lines and normal cell lines

| compound | IC$_{50}$ (μM) | | |
|---|---|---|---|
| | Hela | BGC823 | A549 |
| 14 | 0.92 ± 0.08 | 0.21 ± 0.02 | 1.01 ± 0.14 |
| 15 | 0.60 ± 0.08 | 1.69 ± 0.07 | 2.36 ± 0.23 |
| 16 | 1.56 ± 0.05 | 0.67 ± 0.05 | 1.24 ± 0.33 |
| 17 | 0.97 ± 0.02 | 1.04 ± 0.13 | 1.12 ± 1.74 |
| 18 | 4.14 ± 0.47 | 1.27 ± 0.13 | 4.05 ± 0.15 |
| 19 | 1.51 ± 0.37 | 1.93 ± 1.67 | 0.93 ± 0.84 |
| 20 | 6.62 ± 0.35 | 0.21 ± 0.35 | 0.35 ± 0.37 |
| 21 | 0.52 ± 2.36 | 0.83 ± 0.14 | 5.76 ± 0.18 |
| 22 | 2.31 ± 0.31 | 0.27 ± 0.03 | 1.01 ± 0.38 |
| 23 | 1.22 ± 0.25 | 6.68 ± 0.04 | 2.03 ± 0.45 |
| 24 | 7.18 ± 0.07 | 4.01 ± 0.02 | 1.11 ± 0.94 |
| 25 | 0.73 ± 0.05 | 4.76 ± 0.12 | 2.66 ± 0.27 |
| 26 | 0.25 ± 0.32 | 0.51 ± 0.53 | 4.28 ± 0.11 |
| 27 | 1.33 ± 0.39 | 0.22 ± 0.03 | 3.27 ± 0.17 |
| 28 | 5.26 ± 0.62 | 4.29 ± 0.83 | 1.27 ± 1.12 |
| 29 | 4.57 ± 0.16 | 1.37 ± 0.43 | 0.85 ± 0.93 |
| 30 | 0.51 ± 0.13 | 0.31 ± 0.16 | 1.24 ± 0.27 |
| 31 | 0.13 ± 0.01 | 1.36 ± 0.20 | 1.46 ± 0.89 |
| 32 | 0.53 ± 0.17 | 0.67 ± 0.22 | 1.67 ± 0.28 |
| 33 | 1.56 ± 0.88 | 1.27 ± 0.53 | 1.37 ± 2.15 |
| 34 | 2.11 ± 0.34 | 0.85 ± 0.43 | 5.89 ± 0.74 |
| 35 | 1.19 ± 0.57 | 2.23 ± 0.69 | 0.84 ± 0.62 |
| podophyllotoxin, | 55.53 ± 0.24 | 75.81 ± 0.73 | 67.18 ± 0.24 |
| 4'-demethylepipodophyllotoxins | 49.32 ± 0.38 | 63.09 ± 0.49 | 52.88 ± 0.85 |
| etoposide | 13.15 ± 1.65 | 20.52 ± 2.55 | 20.12 ± 1.95 |

The invention claimed is:

1. A sulfur-substituted podophyllotoxin-type derivative with anti-tumor activity as represented formula (V) or a salt thereof:

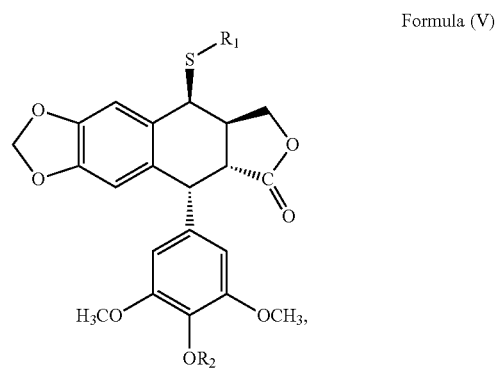

Formula (V)

wherein, R$_1$ is selected from

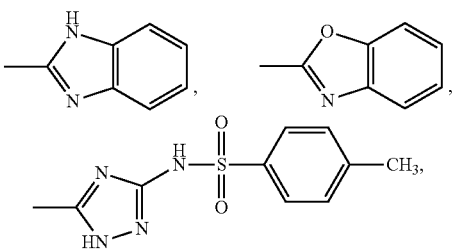

-continued

[chemical structures]

and
R₂ is hydrogen or CH₃.

2. A method for preparing the sulfur-substituted podophyllotoxin-type derivative as claimed in claim 1, comprising steps of:
by nucleophilic substitution reaction, 2-mercaptopyrimidine, 4-amino-2-mercaptopyrimidine, 4,6-dimethyl-2-mercaptopyrimidine, 2-mercaptobenzimidazole or 2-mercaptobenzoxazole being introduced into position 4 of C-ring of podophyllotoxin,
or, by nucleophilic substitution reaction, 2-mercaptopyrimidine, 4-amino-2-mercaptopyrimidine, 4,6-dimethyl-2-mercaptopyrimidine, 2 mercaptobenzimidazole or 2-mercaptobenzoxazole being introduced into position 4 of C-ring of 4'-demethylepipodophyllotoxin.

3. The method as claimed in claim 2, wherein the nucleophilic substitution reaction is carried out under following conditions: podophyllotoxin or 4'-demethylepipodophyllotoxin is dissolved in trifluoroacetic acid, and then 2-mercaptopyrimidine, 4-amino-2-mercaptopyrimidine, 4,6-dimethyl-2-mercaptopyrimidine, 2-mercaptobenzimidazole or 2-mercaptobenzoxazole is added, stirred for reaction, so as to obtain product.

4. The method as claimed in claim 3, wherein, molar ratio between podophyllotoxin or 4'-demethylepipodophyllotoxin and 2-mercaptopyridine, 2-mercapto nicotinic acid, 2-mercapto-6-methylpyridine, 4-mercaptopyridine, 2-mercaptopyrimidine, 4-amino-2-mercaptopyrimidine, 4,6-dimethyl-2-mercaptopyrimidine, 2-mercaptobenzimidazole or 2-mercaptobenzoxazole is 1:1.

5. The method as claimed in claim 2, wherein stirring is performed in vacuo with rotational speed of 50 to 800 rpm, reaction temperature is −20~20° C., reaction time is 1 to 6 hours.

6. The method as claimed in claim 2, comprising:
(1) pouring crude product of Sulfur-etherification-substituted podophyllotoxin derivatives into deionized water with volume of 20~50 times thereof, carrying out precipitation, filtration, filter-cake collection, and 45° C. drying for use;
(2) samples for separation and purification being separated, using silica gel column chromatography and gel column chromatography, sequentially, to obtain product; and
(3) crude product of the sulfonamide podophyllotoxin derivatives being subjected to 35° C. drying by rotary evaporation, then separated, using silica gel column chromatography and reversed-phase column chromatography, sequentially, to obtain product.

7. The method as claimed in claim 6, wherein separation method by silica gel column chromatography comprises: (1) the silica gel column chromatography being normal or reverse phase silica gel column chromatography, wherein normal phase silica gel is mixed in organic solvent with low polarity, loaded into column, balanced with eluent which is preferably formed from chloroform and acetone with volume ratio of 40:1; reverse phase silica gel being mixed with methanol and loaded into column, balanced with eluent which is formed from methanol and water with volume ratio of 60:1; (2) samples for separation and purification being dissolved with the eluent, subjected to sample adsorption, then eluted with eluent which is collected later, then the sample being evaporated to dryness and recrystallized; and
separation method by gel column chromatography comprises: (1) soaking the gel in methanol; loading processed gel into column and balanced with methanol; (2) sample preliminary separated by silica gel column chromatography being dissolved in methanol, subjected to sample absorption, and then eluated with eluent which is collected later, then the sample being evaporated to dryness and recrystallized.

8. An anti-tumor pharmaceutical composition, comprising a compound of formula (V) or a salt thereof as claimed in claim 1 with effective amount in treatment, and a pharmaceutically acceptable carrier thereof.

9. The method as claimed in claim 3, wherein stirring is performed in vacuo with rotational speed of 50 to 800 rpm, reaction temperature is −20~20° C., reaction time is 1 to 6 hours.

10. The method as claimed in claim 4, wherein stirring is performed in vacuo with rotational speed of 50 to 800 rpm, reaction temperature is −20~20° C., reaction time is 1 to 6 hours.

11. The method as claimed in claim 5, wherein rotational speed of the stirring is 600 rpm, reaction temperature is −10~10° C., and reaction time is 1 hour.

* * * * *